US008986365B2

(12) United States Patent
Bowe

(10) Patent No.: US 8,986,365 B2
(45) Date of Patent: Mar. 24, 2015

(54) DELIVERY SYSTEM WITH RETRACTABLE PROXIMAL END

(75) Inventor: Jason S. Bowe, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 264 days.

(21) Appl. No.: 13/515,563

(22) PCT Filed: Dec. 9, 2010

(86) PCT No.: PCT/US2010/059661
§ 371 (c)(1),
(2), (4) Date: Jul. 23, 2012

(87) PCT Pub. No.: WO2011/084342
PCT Pub. Date: Jul. 14, 2011

(65) Prior Publication Data
US 2012/0277845 A1 Nov. 1, 2012

Related U.S. Application Data

(60) Provisional application No. 61/287,511, filed on Dec. 17, 2009.

(51) Int. Cl.
A61F 2/06 (2013.01)
A61M 25/00 (2006.01)
(Continued)

(52) U.S. Cl.
CPC ............. *A61M 25/0068* (2013.01); *A61F 2/95* (2013.01); *A61M 25/0074* (2013.01); *A61F 2/07* (2013.01);
(Continued)

(58) Field of Classification Search
CPC ..... A61F 2/95; A61F 2/958; A61F 2002/011; A61F 2250/0003; A61F 2/2433; A61M 25/10; A61M 25/104; A61M 25/1002; A61M 2025/1093; A61M 2025/1004

USPC ............... 604/96.01, 103.08, 103.09, 103.13, 604/103.14, 164.01, 164.03; 606/108; 623/1.11, 1.12, 1.23
See application file for complete search history.

(56) References Cited

U.S. PATENT DOCUMENTS 4,083,369 A * 4/1978 Sinnreich ................. 604/103.06
5,254,091 A * 10/1993 Aliahmad et al. ....... 604/103.06
(Continued)

FOREIGN PATENT DOCUMENTS

FR 2 860 705 4/2004
WO WO 2004/006804 1/2004

OTHER PUBLICATIONS

International Search Report completed Mar. 15, 2011 for the International Application No. PCT/US2010/059661, 5 pgs.
(Continued)

Primary Examiner — Jonathan W Miles
(74) Attorney, Agent, or Firm — Brinks Gilson & Lione

(57) ABSTRACT

A medical device delivery system is described, the medical device delivery system comprising: a medical device carrier portion comprising a proximal end; a release mechanism cooperating with said medical device carrier portion and operable to release a medical device from said medical device carrier portion; and a proximal tip portion. The proximal tip portion comprises a largest outside diameter, a proximal end, a distal end, and a plurality of longitudinal lengths as measured from said proximal end to said distal end of said proximal tip portion, and is disposed proximal to said medical device carrier portion. The proximal tip portion further comprises and is operable between at least an extended longitudinal length and a retracted longitudinal length of said plurality of longitudinal lengths. Said extended longitudinal length is greater than said retracted longitudinal length.

20 Claims, 21 Drawing Sheets

(51) Int. Cl.
*A61F 2/95* (2013.01)
*A61F 2/07* (2013.01)
*A61F 2/958* (2013.01)
*A61M 29/02* (2006.01)
*A61M 25/01* (2006.01)
*A61M 25/06* (2006.01)

(52) U.S. Cl.
CPC ......... *A61F 2/958* (2013.01); *A61F 2250/0018* (2013.01); *A61F 2250/0036* (2013.01); *A61F 2250/0065* (2013.01); *A61M 25/0023* (2013.01); *A61M 25/0054* (2013.01); *A61M 25/0069* (2013.01); *A61M 29/02* (2013.01); *A61M 2025/0079* (2013.01); *A61M 2025/0081* (2013.01); *A61M 2025/0175* (2013.01); *A61M 2025/0681* (2013.01)
USPC ...................................................... 623/1.11

(56) References Cited

U.S. PATENT DOCUMENTS

| | | | |
|---|---|---|---|
| 5,344,426 A | 9/1994 | Lau et al. | |
| 5,797,947 A * | 8/1998 | Mollenauer | 606/192 |
| 5,957,974 A * | 9/1999 | Thompson et al. | 623/1.13 |
| 6,048,332 A * | 4/2000 | Duffy et al. | 604/103.08 |
| 6,746,424 B2 * | 6/2004 | Stamberg | 604/103.06 |
| 6,960,186 B1 * | 11/2005 | Fukaya et al. | 604/103.06 |
| 7,025,745 B2 * | 4/2006 | Lim et al. | 604/103.06 |
| 7,175,607 B2 * | 2/2007 | Lim et al. | 604/103.06 |
| 7,201,770 B2 * | 4/2007 | Johnson et al. | 623/1.12 |
| 7,753,875 B2 * | 7/2010 | Burton | 604/103.06 |
| 7,967,798 B2 * | 6/2011 | Reydel et al. | 604/271 |
| 7,972,369 B2 * | 7/2011 | Kaplan et al. | 623/1.12 |
| 8,034,022 B2 * | 10/2011 | Boatman | 604/96.01 |
| 8,361,017 B2 * | 1/2013 | Rickert et al. | 604/103.14 |
| 2002/0072707 A1 * | 6/2002 | Gonzalez et al. | 604/103.06 |
| 2003/0105508 A1 * | 6/2003 | Johnson et al. | 623/1.11 |
| 2003/0125751 A1 | 7/2003 | Griffin et al. | |
| 2003/0135258 A1 * | 7/2003 | Andreas et al. | 623/1.11 |
| 2004/0176791 A1 * | 9/2004 | Lim et al. | 606/194 |
| 2004/0199177 A1 | 10/2004 | Kim | |
| 2004/0267197 A1 * | 12/2004 | Blankenship | 604/103.06 |
| 2005/0043679 A1 * | 2/2005 | Devens et al. | 604/103.06 |
| 2006/0025844 A1 * | 2/2006 | Majercak et al. | 623/1.11 |
| 2007/0118076 A1 * | 5/2007 | Lim et al. | 604/103.06 |
| 2008/0051821 A1 | 2/2008 | Gephart | |
| 2008/0177228 A1 * | 7/2008 | Burton | 604/103.06 |
| 2008/0255652 A1 | 10/2008 | Thomas et al. | |
| 2009/0234279 A1 | 9/2009 | Goldstein | |
| 2009/0247945 A1 * | 10/2009 | Levit et al. | 604/103 |
| 2010/0152654 A1 * | 6/2010 | Tilson et al. | 604/103.06 |
| 2011/0224771 A1 * | 9/2011 | Schwager | 623/1.11 |

OTHER PUBLICATIONS

Written Opinion of the International Searching Authority, mailed Mar. 15, 2011, for the International Application No. PCT/US2010/059661, 9 pgs.

* cited by examiner

DELIVERY SYSTEM WITH RETRACTABLE PROXIMAL END

RELATED APPLICATIONS

The present patent document is a §371 filing based on PCT Application Serial No. PCT/US2010/059661, filed Dec. 9, 2010 (and published as WO 2011/084342 A1 on Jul. 14, 2011), designating the United States and published in English, which claims the benefit of the filing date under 35 U.S.C. §119(e) of Provisional U.S. Patent Application Ser. No. 61/287,511, filed Dec. 17, 2009. All of the foregoing applications are hereby incorporated by reference in their entirety.

TECHNICAL FIELD

The present invention relates generally to intravascular medical devices, in particular a delivery system for endoluminally accessing the vasculature for human or animal patients.

BACKGROUND ART

Endoluminal systems have been developed for implanting medical devices in patients, specifically in the thoracic aorta. Some of these medical devices are implanted in the ascending or descending aorta.

DISCLOSURE OF THE INVENTION

A medical device delivery system is made up of at least a medical device carrier portion which has a proximal end; a release mechanism cooperating with the carrier portion and is operable to release a medical device from the carrier portion; and a proximal tip portion which has a proximal end and is positioned proximal to the medical device carrier portion. The proximal tip portion further comprises and is operable between an extended longitudinal length and various retracted longitudinal lengths. The extended longitudinal length is greater than the retracted longitudinal lengths. The proximal end of the medical device carrier portion becomes longitudinally closer to the proximal end of the proximal tip portion when the proximal tip portion is operated toward the retracted longitudinal lengths. In addition, the largest outside diameter of the proximal tip portion does not substantially increase when proximal tip portion is operated from the extended longitudinal length toward the retracted longitudinal length.

The proximal tip portion may further contain an interior void and the medical device carrier portion may also have a lumen extending longitudinally through the carrier portion. The interior void communicates with the medical device carrier portion lumen. The interior void may be in fluid communication with the medical device carrier portion lumen. The proximal tip portion transitions between the extended longitudinal length and the various retracted longitudinal lengths upon a change in volume of the interior void. The proximal tip portion may further comprise a non-distensible balloon.

The delivery system may also have a mechanical actuator, which transitions the proximal tip portion between the extended longitudinal length and the retracted longitudinal lengths. The mechanical actuator may contain a lumen which may be suitable for a medical device such as a wire guide.

At least part of delivery system, such as the proximal tip portion, may be radiopaque. The largest outside diameter of the proximal tip portion at the extended longitudinal length may be substantially the same as the largest outside diameter of the proximal tip portion at various retracted longitudinal lengths. The largest outside diameter of the proximal tip portion at the retracted longitudinal lengths may be smaller than at the extended longitudinal length. Furthermore, the largest outside diameter of the proximal tip portion may be equal to or less than the inside diameter of a medical device containment sheath.

A medical device, such as a stent, graft, or stent-graft, may be positioned within the lumen of a containment sheath, concentric and/or coaxial to the carrier portion, near the proximal end of the carrier portion. The stent or stent-graft may be self-expanding or balloon expandable.

The proximal tip portion may further comprise undulations or pleats, variations in wall thickness, variations in wall stiffness, or inserts, encouraging the proximal tip portion to be arranged in a predetermined configuration when it is at the retracted longitudinal lengths.

A method of delivering a medical device may comprise:
providing a medical device delivery system;
locating the proximal tip portion in a patient, proximate a treatment site, the proximal tip portion in its extended longitudinal length; and
operating the proximal tip portion from its extended longitudinal length to its retracted longitudinal length.

Preferably the method further comprises:
providing a medical device on the medical device carrier portion of the medical device delivery system; and
releasing the medical device from the medical device carrier portion.

Advantageously, the method is performed during the implantation of a medical device at or proximate the heart of a patient.

The tip may be in its extended longitudinal length for tracking through the vasculature. Once the proximal tip portion is located proximate a treatment site the proximal tip portion may be retracted. The medical device carrier portion may then be advanced closer to the treatment site. Thus, retraction of the tip may enable the medical device carrier portion to be positioned closer to a first area of a vessel than with it could be with the proximal tip portion in an extended configuration. In this way, areas of the vessel which may not be treatable with an extended proximal tip portion may be treatable with the proximal tip portion at a retracted longitudinal length.

DETAILED DESCRIPTION OF THE INVENTION

Throughout the specification, in the embodiments generally shown herein, "proximal" as used herein, shall generally refer to being closest to the heart 25, and "distal" as used herein, shall generally refer to being furthest from the heart 25.

Figure 1:
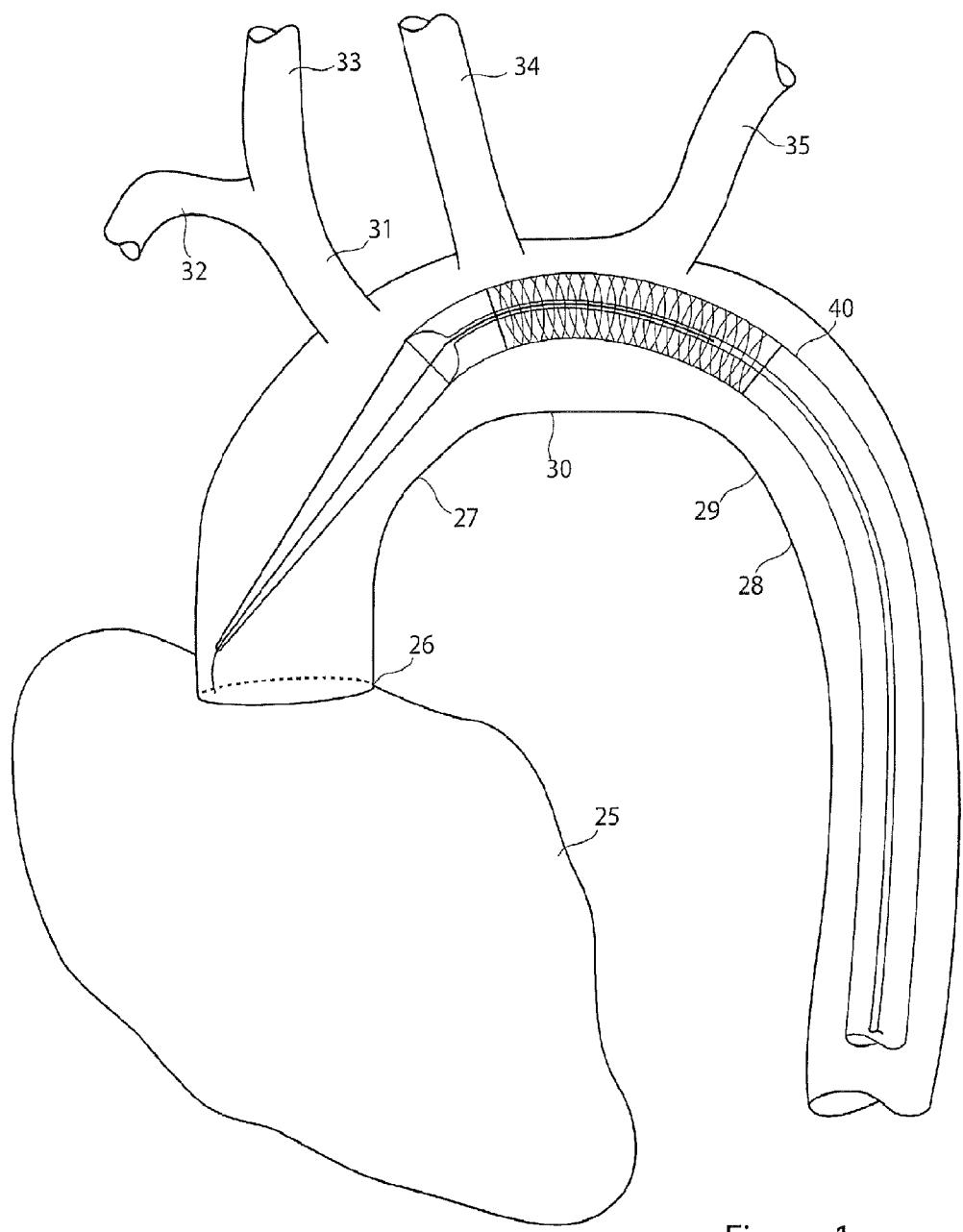
FIG. 1 is a front schematic view of an exemplary ascending and descending thoracic aorta with a proximal-most end of an exemplary delivery system close to, but not crossing, the aortic valve.

FIG. 1 illustratively depicts a front schematic view of the thoracic aorta 29, including the ascending thoracic aorta 27, the descending thoracic aorta 28, the aortic arch 30, the aortic valve 26, and the heart 25. At least three arteries, including the left subclavian artery 35, the left common carotid artery 34, and the brachiocephalic artery 31, branch from the aortic arch 30. The brachiocephalic artery 31 includes the right subclavian artery 32 and the right common carotid artery 33. FIG. 1 also depicts a medical device delivery system 40 placed within the thoracic aorta 29 for placement of devices including stents, grafts, stent-grafts, and other medical devices within an area of the thoracic aorta 29.

Figure 2:
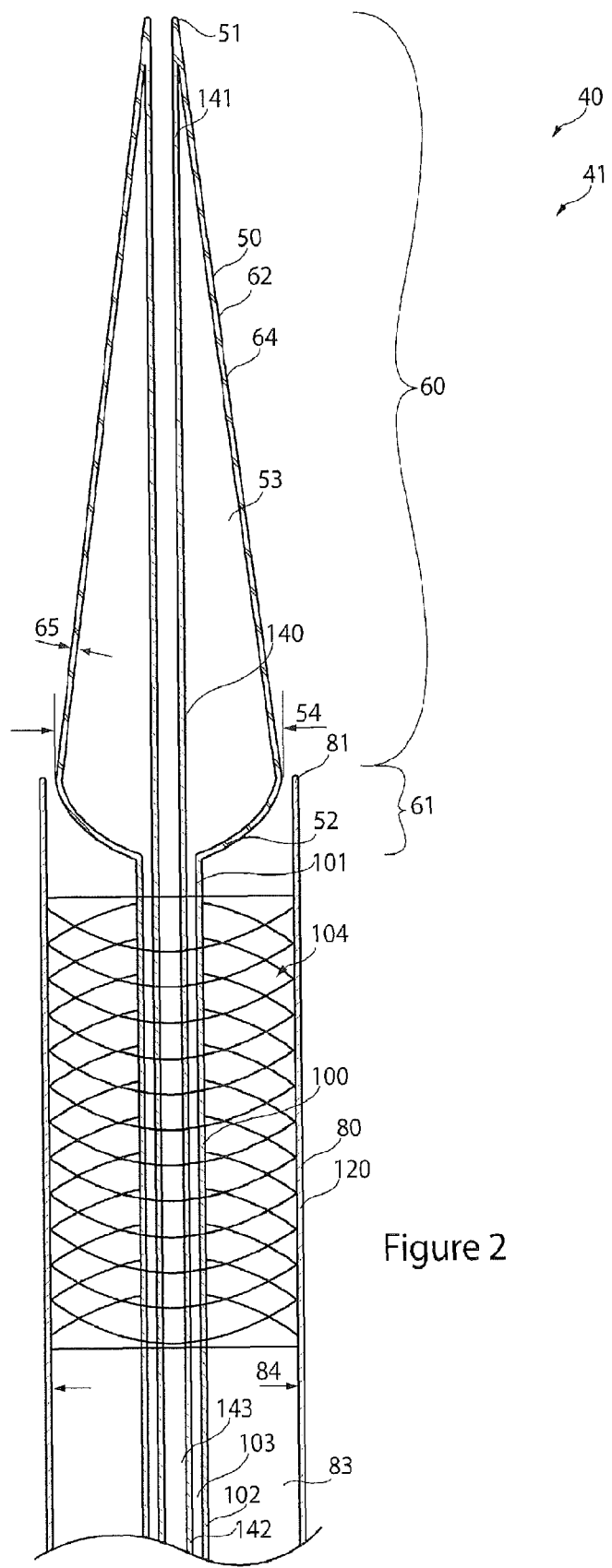
FIG. 2 is a side schematic view of a medical device delivery system with retractable proximal end at an extended longitudinal length. Also depicted is an optional medical device containment sheath.

As depicted in FIGS. 1 and 2, the delivery system 40, in one embodiment, includes a proximal end 41 and a proximal tip portion 50 at the proximal end 41 of the delivery system 40. The proximal tip portion 50 assists in the smooth introduction of the delivery system 40 into the vasculature of a patient. As depicted in FIG. 1, the delivery system 40 also includes a medical device carrier portion 100 and a medical device 104 to be placed in the thoracic aorta 29. As depicted in FIG. 1, the delivery system 40 has been advanced through the thoracic aorta 29 such that the medical device carrier portion 100 lies within the aortic arch 30 and the proximal tip portion 50 lies in close proximity to the aortic valve 26. In this configuration, further advancement of the delivery system 40 to place the medical device 104 closer to the aortic valve 26, may result in the proximal tip portion 50 passing through the aortic valve 26 and into the heart 25.

FIG. 2 is a partial view of the proximal end 41 of an exemplary delivery system 40. As depicted, the delivery system 40 has a proximal end 41 and a proximal tip portion 50 at the proximal end 41. The proximal tip portion 50 may be tapered and also may have a reverse taper at its distal end, as depicted in FIG. 2. The proximal tip portion 50 lies proximal of and may be connected to the medical device carrier portion 100 upon which a medical device 104, such as a stent, a graft, or stent-graft, is concentrically disposed. In one embodiment, the medical device carrier portion 100 comprises an inner cannula having a lumen 103 that may accommodate one or more wire guides, or other implements, and/or may permit the introduction of contrast fluid therethrough. In the embodiment depicted in FIG. 2, the medical device carrier portion 100 has a diameter that is smaller than the diameter of the proximal tip portion 50.

Depending on the type of application, the delivery system also may include a sheath 80 surrounding the medical device carrier portion 100 and the medical device 104. The sheath 80 operates to hold the medical device 104, for example in the case of a self-expanding prosthesis, in a compressed configuration until retraction of the sheath permits the medical device to expand. Other mechanisms (not shown), such as trigger wires and the like also may be employed to hold the device in place. The sheath 80 may have an inner diameter 84 at its proximal end 81 that approximates an outer diameter 54 of the distal end 52 of the proximal tip portion 50 and may engage the distal end 52 of the proximal tip portion 50. The carrier portion 100 may be disposed partially or entirely within the sheath lumen and may move longitudinally therein. In other embodiments, such as in the case of balloon expandable stents, a sheath may not be necessary.

The proximal tip portion 50 may be either radially or axially collapsible, or both, to accommodate the anatomy of the patient. As used here, the term "collapsible" also means retractable, for example by means of a telescoping relationship. In the first embodiment, at least a portion of the diameter of the tip is reduced. In the second embodiment, the longitudinal length of the proximal tip portion is reduced. In the second embodiment, however, the diameter of the proximal tip portion does not increase substantially beyond the largest diameter of the proximal tip portion at the extended longitudinal length.

In some embodiments, the proximal tip portion may be radially compressed in situations where a reduced radial profile of the proximal tip portion is desired. For example, in some situations, it may be necessary to advance the tip past the aortic valve to place the medical device. Compression of the proximal tip portion reduces the radial profile of the tip permitting it to pass through the valve without dilation or damage to the valve. In this embodiment, the delivery system may be advanced further into the vasculature to place the proximal end of the medical device closer to the valve. Radial compression of the proximal tip portion may be achieved by, for example, fluid actuation. If a flexible proximal tip portion is sealed and fluid contained within the tip is withdrawn from the tip, the tip will be radially compressed.

In another embodiment, the proximal tip portion may be longitudinally retractable between an extended longitudinal length and one or more shorter, retracted longitudinal lengths. In this embodiment, illustratively depicted in FIG. 3, the length of the proximal tip portion is shortened to avoid abutting against or passing through the aortic valve, while at the same time permitting the delivery system to advance further into the ascending aorta for placement of the medical device closer to the aortic valve.

Figure 8:
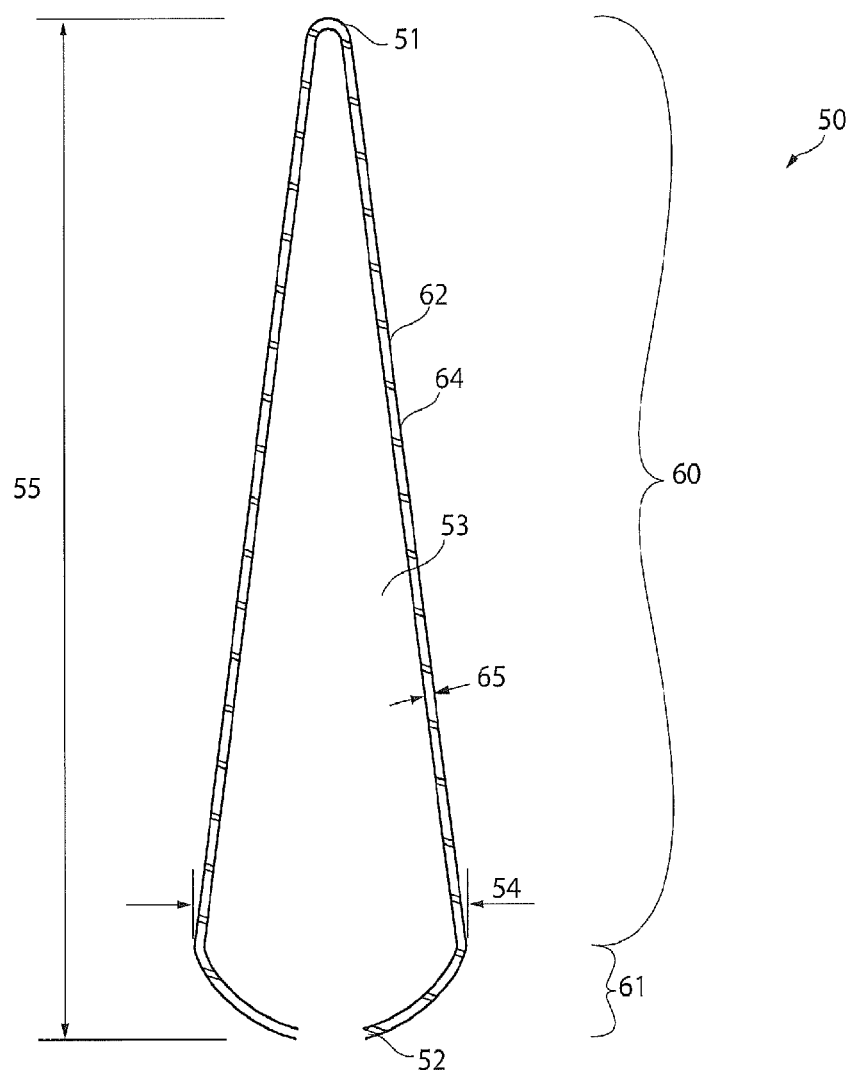
FIG. 8 is a side schematic view of one exemplary proximal tip portion at the extended longitudinal length. The release mechanism and medical device carrier portion have been omitted for clarity of presentation.
Figure 9:
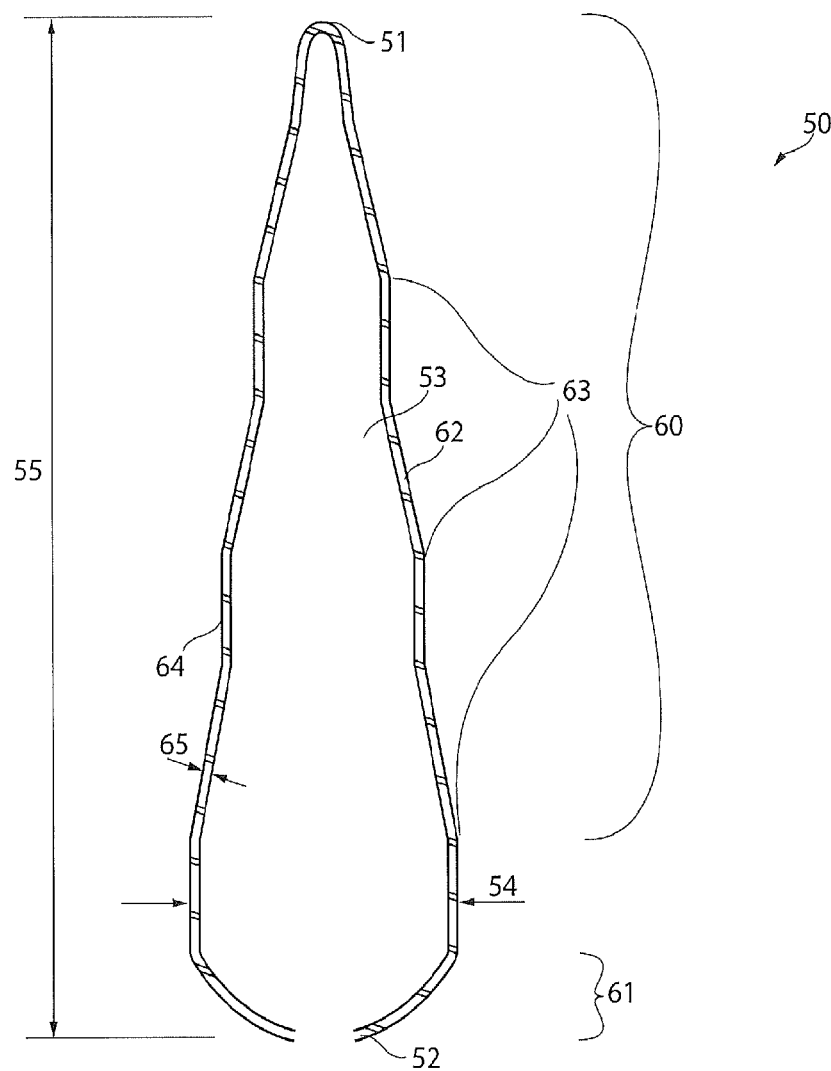
FIG. 9 is a side schematic view of an embodiment of a proximal tip portion at the extended longitudinal length with the wall of the proximal tip portion exhibiting undulations. The release mechanism and medical device carrier portion have been omitted for clarity of presentation.
Figure 10:
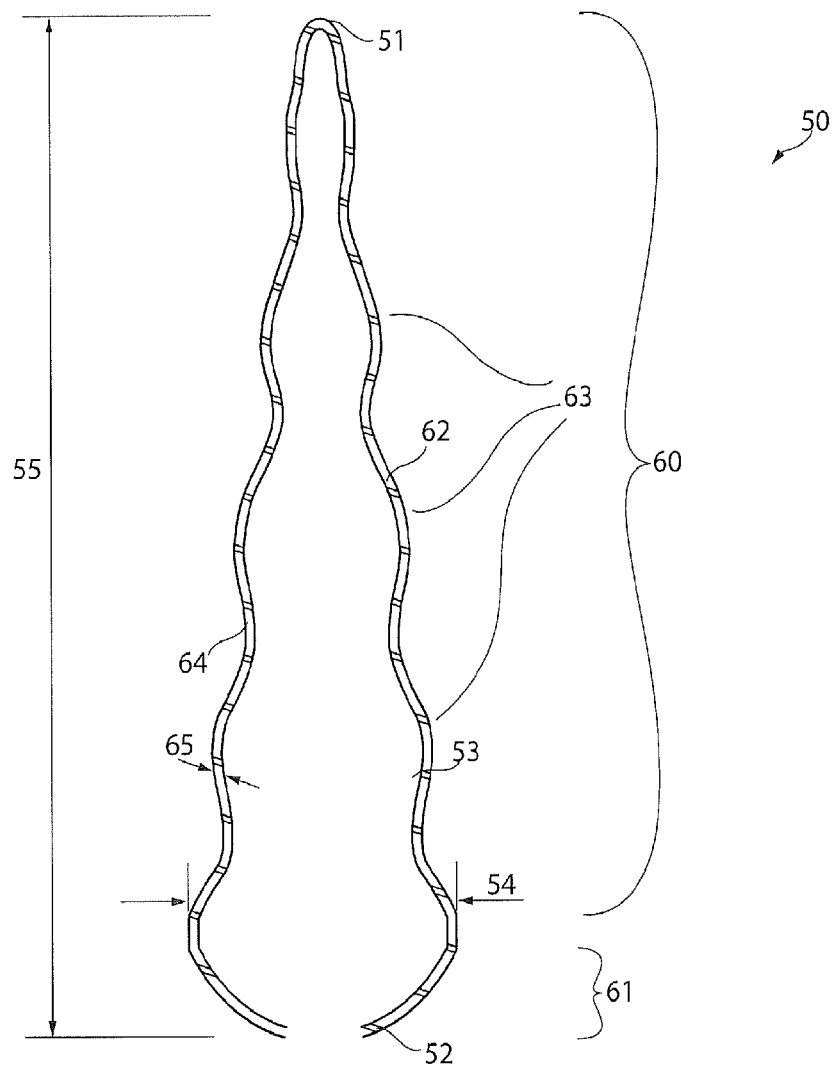
FIG. 10 is a side schematic view of an embodiment of a proximal tip portion at the extended longitudinal length with the wall of the proximal tip portion exhibiting undulations. The release mechanism and medical device carrier portion have been omitted for clarity of presentation.

FIG. 2 depicts a partial view of an exemplary delivery system 40. In this example, the delivery system 40 includes a medical device carrier portion 100, a medical device containment sheath 80, a release mechanism 120, and a proximal tip portion 50. As depicted, the proximal tip portion 50 has a proximal end 51 and a distal end 52 and is disposed proximal to the carrier portion 100. The longitudinal length of the proximal tip portion 50, as measured from the proximal end 51 to the distal end 52, may decrease. The proximal tip portion 50 at a diminished longitudinal length may be arranged in a predetermined configuration, as shown in FIGS. 11 to 14, with a single set of folds 56; multiple sets of folds generally flush with each other 57, 58; or multiple sets of folds that are not flush with each other 59. The proximal tip portion 50 is operable between the extended longitudinal length 55, as shown in FIGS. 8 to 10, and retracted longitudinal lengths 56, 57, 58, 59. The extended longitudinal length 55 is greater than the retracted longitudinal lengths 56, 57, 58, 59.

In an embodiment, one function of the delivery system 40 is to allow a medical device 104, such as the Zenith TX2 TAA Endovascular Graft available from Cook Medical in Bloomington, Ind., or another commercially available stent-graft, to be inserted into a vessel intraluminally to treat a thoracic aortic aneurysm. In one method of use, the proximal tip portion 50 remains at the extended longitudinal length 55 until the proximal tip portion 50 becomes close to an obstruction, for example, in the case of the thoracic aorta, the aortic valve 26. Other obstructions may impede progress of the delivery system 40 when it is used in other contexts.

The proximal tip portion 50 may be retracted to a shorter length to avoid contact with the obstruction. When doing so, the proximal end 101 of the carrier portion 100 may move closer to the proximal end 51 of the proximal tip portion 50. The delivery system 40, and any associated medical device, may be advanced closer to, for example, the aortic valve 26 after the proximal tip portion 50 has been retracted without coming into contact with, and possibly damaging the valve.

The containment sheath 80 may move independently of the carrier portion 100 and the proximal tip portion 50. The proximal end 81 of the containment sheath 80 may be longitudinally in front of, behind, or flush with the proximal end 51 of the proximal tip portion 50. If the proximal end 81 of the containment sheath 80 is closer to the aortic valve 26 than the proximal end 51 of the proximal tip portion 50, the containment sheath 80 may need to be retracted distally before the carrier portion 100 is advanced toward the aortic valve 26. Because the containment sheath 80 may be at least part of the release mechanism 120, the containment sheath 80 may need to withdraw further to deploy the medical device.

The medical device containment sheath 80 may be a generally cylindrical sheath with at least one lumen 83 extending longitudinally therein. In one embodiment, the diameter of the lumen 83 is substantially constant throughout the sheath. The proximal end 81 of the containment sheath 80 need not be drawn back prior to the proximal tip portion 50 transitioning from the extended longitudinal length 55 to the retracted longitudinal lengths 56, 57, 58, 59 as shown in FIGS. 11 to 14. The inside diameter 84 of the containment sheath 80 should be large enough to accommodate at least part of the carrier portion 100 as well as any medical device 104 coupled thereto.

The containment sheath 80 may comprise a flexible, tubular member that may be formed from one or more semi-rigid polymers. For example, the containment sheath 80 may be manufactured from polyurethane, polyethylene, tetrafluoroethylene, polytetrafluoroethylene, fluorinated ethylene propylene, nylon, PEBAX, equivalents, or adequate substitutions. One example of the containment sheath 80 is the kink-resistant Flexor Introducer Sheath available from Cook Medical in Bloomington, Ind., and typically ranges in size from 16 to 22 French.

In order for the proximal end of the delivery system 40 to reach the thoracic aorta 29, it must first be introduced into an arterial vessel, such as the femoral artery. From there, a physician can navigate it through vessels which are often partially occluded and/or tortuous or neither. It is desirable that the medical device 104 not be damaged during the period of insertion and navigation, and thus the containment sheath 80 may serve to protect the medical device 104 from external damage. The medical device 104 may comprise a stent-graft 105, a self-expanding stent-graft 106, or a balloon expandable stent 107. In the case where the medical device 104 comprises a self-expanding stent graft 106, the containment sheath 80 may also serve to keep the self-expanding stent graft 106 from deploying and expanding prematurely. Other medical devices may be used with the delivery system 40 with or without the containment sheath 80.

In the preferred embodiment, the proximal end 101 is the closest part of the carrier portion 100 to the proximal end 51 of the proximal tip portion 50. The proximal end 101 of the carrier portion 100 may be attached or affixed or otherwise coupled to the distal end 52 of the proximal tip portion 50. Other embodiments may benefit from the proximal end 101 of the carrier portion 100 being not attached to the distal end 52 of the proximal tip portion 50.

If the delivery system 40 comprises a containment sheath 80, then the carrier portion 100 is disposable within the lumen 83 of, is separate from, and is movable independently of the containment sheath 80. Operation of the containment sheath 80 does not necessarily require operation of the carrier portion 100. The outside diameter of the carrier portion 100 should be such that it can move within the lumen 83 of the containment sheath 80 without undue resistance.

As depicted in FIG. 2, the carrier portion 100 may further comprise a lumen 103 extending longitudinally therein. Said lumen 103 may be sized appropriately to adequately accommodate a fluid actuator, a mechanical actuator 140 which optionally has a lumen 143 extending longitudinally therein, or any combination thereof. In one embodiment, the lumen 103 of the carrier portion 100 is sized to accommodate the mechanical actuator 140 with a lumen 143 extending longitudinally therein, leaving enough room between the outside of the mechanical actuator 140 and the inside of the carrier portion 100 to allow fluid to pass through at least part of the lumen 103 of the carrier portion 100.

In the preferred embodiment, the medical device 104 may be coupled to the carrier portion 100. However, other embodiments may allow a medical device to be coupled to or associated with part of the proximal tip portion 50, the containment sheath 80, or other parts of the delivery system 40. The carrier portion 100 may comprise a plurality of medical devices. The plurality of medical devices, disposed substantially coaxial to the carrier portion 100, may be disposed radially or longitudinally in relation to other medical devices 104 of the plurality.

The release mechanism 120 may be disposed on the proximal tip portion 50, the containment sheath 80, the carrier portion 100, or some other part of the delivery system 40. One function of the release mechanism 120 is to release, deploy, detach, expand, or decompress at least part of the medical device 104.

An exemplary embodiment comprising the release mechanism 120 comprises a set of trigger wires (not shown) used to compress a proximal end of a self-expanding medical device 106. Such trigger wires can be found in U.S. Patent Publication No. U.S. 2003/0233140 and is hereby incorporated by reference in its entirety.

An embodiment comprising the release mechanism 120 may comprise an expandable balloon, for instance, one used with balloon expandable stents. Such an expandable balloon can be found in U.S. Pat. No. 6,592,592 and is hereby incorporated by reference in its entirety. Examples of balloon expandable stents 107 may be found in the same reference. Optionally, this balloon expandable stent may have a covering and need not be bare.

Another embodiment, illustratively depicted in FIG. 2, comprising the release mechanism 120 may comprise the containment sheath 80. In this embodiment, the containment sheath 80 may be used to prevent the self-expanding stent-graft 106 from deploying prematurely. The release mechanism 120 (not shown) may further comprise part of the carrier portion 100 such that when the containment sheath 80 is withdrawn distally, that the medical device 104, coupled with the carrier portion 100, does not withdraw distally as well. Withdrawing the containment sheath 80 may therefore expose a proximal end of the medical device 104, which may then expand and deploy. Withdrawing the containment sheath 80 further will expose more of the medical device 104 and may expose the remainder of said device. With no containment sheath surrounding the medical device 104, said device may be free to expand within the vessel. The containment sheath 80 may be used with medical devices other than self-expanding stent-grafts 106. The containment sheath 80 may also be used in conjunction with release mechanism 120. Furthermore, additional release mechanisms may be compatible with the delivery system 40 and non-disclosure herein does not prevent them from being adequate substitutions.

The proximal tip portion 50 may be operated independently of the carrier portion 100 and the containment sheath 80. The largest outside diameter 54 of the proximal tip portion 50 at the extended longitudinal length 55 may be equal to or less than the inside diameter 84 of the containment sheath 80, as depicted in FIG. 2, such that the proximal tip portion 50 may be withdrawn into the containment sheath 80. However, other embodiments may benefit from the largest outside diameter 54 of the proximal tip portion 50 being greater than the inside diameter 84 of the containment sheath 80.

The proximal tip portion 50 further comprises a first tapered portion 60 and a second tapered portion 61. In one embodiment, the largest outside diameter 54 of the proximal tip portion 50 is at the longitudinal intersection of the first tapered portion 60 and the second tapered portion 61; however, it is not required that these two portions intersect or share a common annular ring, as depicted in FIG. 9.

In one embodiment, the proximal tip portion 50 may further comprise a wall 62, and an interior void 53, wherein said interior void 53 communicates with the lumen 103 of the carrier portion 100. The interior void 53 is at least partially filled with a fluid enabling the volume of the interior void 53 to change. A change in volume may be accomplished either by removing fluid from the interior void 53 through the lumen 103 of the carrier portion 100 or through a different outlet, or by changing the density of the fluid contained within the interior void 53 such that the volume of the interior void 53 changes. The interior void 53 need not occupy the majority, or even a significant fraction of the proximal tip portion 50; the interior void 53 need only occupy enough of the proximal tip portion 50 such that when the volume of the interior void 53 changes, the proximal tip portion 50 transitions from an extended longitudinal length 55 toward the retracted longitudinal lengths 56, 57, 58, 59 as shown in FIGS. 11 to 14.

Figure 7:
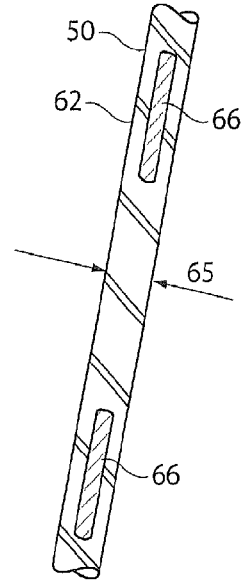
FIG. 7 is an exploded side schematic view of a proximal tip portion with constant wall thickness and inserts contained within the wall resulting in longitudinal variations in wall stiffness.

The structure of the proximal tip portion 50 may comprise features that encourage the proximal tip portion 50 at the retracted longitudinal lengths 56, 57, 58, 59 to be arranged in a predetermined configuration. These features may include any, all, or none of the following: variations in wall thickness 65, the proximal tip portion 50 wall 62 exhibiting undulations 63 or pleats, variations in wall stiffness, and/or annular inserts 66, as shown in FIG. 7. Depending on the specific desired shape of the proximal tip portion 50, none of the aforementioned features may be necessary to encourage the proximal tip portion 50 at the retracted longitudinal lengths 56, 57, 58, 59 to be arranged in a predetermined configuration.

Figure 4:
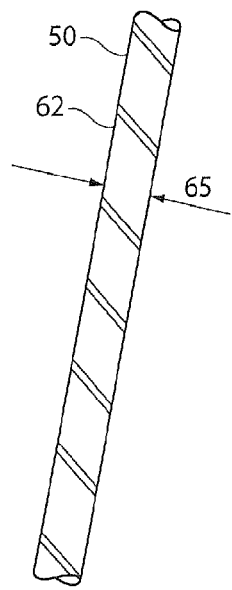
FIG. 4 is an exploded side schematic view of a proximal tip portion with constant wall thickness and constant wall stiffness.
Figure 5:
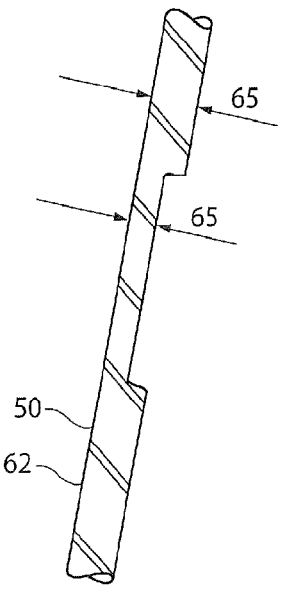
FIG. 5 is an exploded side schematic view of a proximal tip portion with longitudinal variations in wall thickness.

An exemplary proximal tip portion 50 comprising a uniform wall thickness 65 and uniform wall stiffness is illustratively depicted in FIG. 4. Contrastingly, an exemplary proximal tip portion 50 with a non-uniform wall thickness 65 is illustratively depicted in FIG. 5. Here, some annular sections of the proximal tip portion 50 may have a reduced wall thickness 65; therefore, these annular sections may be less stiff than the annular sections having a non-reduced wall thickness 65. Varying the wall thickness 65 of the proximal tip portion 50 may encourage the proximal tip portion 50 at the retracted longitudinal lengths 56, 57, 58, 59 to be arranged in a predetermined configuration.

Figure 6:
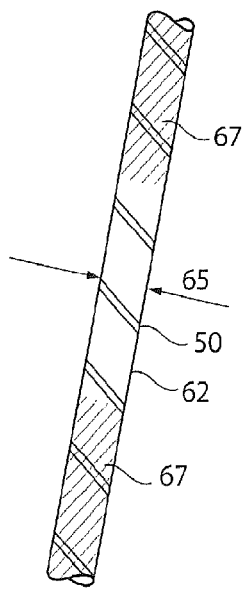
FIG. 6 is an exploded side schematic view of a proximal tip portion with constant wall thickness and variations in wall stiffness.

An exemplary proximal tip portion 50 comprising a uniform wall thickness 65 and annular sections having modified stiffness 67 is illustratively depicted in FIG. 6. Annular sections wherein the stiffness has been modified 67 may be accomplished by using a different material, a different composition of the same material, heat treatment, chemical treatment, exposure to electromagnetic radiation, etc. As well, the proximal tip portion 50 comprising a uniform wall thickness 65 illustratively depicted in FIG. 7 comprises a uniform wall thickness 65; however, it differs because this embodiment achieves a longitudinally non-uniform stiffness by utilizing inserts 66 in the wall 62 of the proximal tip portion 50. Inserts 66 comprising stiffer materials (e.g. plastic, rubber, metal) may increase the stiffness of these sections. Inserts 66 comprising less stiff materials (e.g. gas, liquid, gel, foam) may decrease the stiffness of these sections. Inserts 66 may be disposed within the wall 65 of the proximal tip portion 50 or on the interior or exterior surface of the wall 65 of the proximal tip portion 50.

The largest outside diameter 54 of the proximal tip portion 50 at the retracted longitudinal lengths may be substantially equal to, i.e. equal to, greater than, or smaller than, the largest outside diameter 54 of the proximal tip portion 50 at the extended longitudinal length 55. Where the largest outside diameter 54 of the proximal tip portion 50 at the retracted longitudinal lengths is greater than the largest outside diameter 54 of the proximal tip portion 50 at the extended longitudinal length 55, it may be not substantially greater. Where the largest outside diameter 54 of the proximal tip portion 50 at the retracted longitudinal lengths is smaller than the largest outside diameter 54 of the proximal tip portion 50 at the extended longitudinal length 55, it may be not substantially smaller.

In some cases, the largest outside diameter 54 of the proximal tip portion 50 at the retracted longitudinal lengths may not be substantially larger than the largest outside diameter 54 of the proximal tip portion 50 at the extended longitudinal length 55. Furthermore, the outside diameter 54 may decrease as the proximal tip portion 50 transitions from the extended longitudinal length 55 to the retracted longitudinal lengths 56, 57, 58, 59. Because the proximal outside diameter 54 of the proximal tip portion 50 does not significantly increase, there is less risk of the proximal tip portion 50 getting caught on the medical device 104 as it is deployed. In certain instances, it may be advantageous for the proximal tip portion 50 and carrier portion 100 to be used with a medical device containment sheath 80 and for the proximal tip portion 50 and carrier portion 100 to be partially or fully withdrawn distally through the containment sheath 80 during a medical procedure. Were the outside diameter 54 of the proximal tip portion 50 to significantly increase upon retraction, it would be less likely that the proximal tip portion 50 and carrier portion 100 would be able to be withdrawn through the containment sheath 80. Even during medical procedures not requiring a containment sheath 80, there may still be advantages to having a proximal tip portion 50 that does not significantly increase in diameter when longitudinally retracted.

In other instances, it may be beneficial for the outside diameter of the proximal tip portion to decrease upon transitioning from the extended longitudinal length toward the retracted longitudinal lengths.

In other instances, it may be beneficial for the largest outside diameter 54 of the proximal tip portion 50 to increase upon transitioning from the extended longitudinal length toward the retracted position. In particular the largest outside diameter 54 of the proximal tip portion 50 may increase slightly upon transitioning from the extended longitudinal length toward the retracted position such that the largest outside diameter 54 of the proximal tip portion 50 in the retracted position is slightly larger than the largest outside diameter 54 of the proximal tip portion 50 in the extended position. In this case the increased largest outside diameter 54 of the proximal tip portion 50 may be beneficial to protect the open end of a sheath if repositioning of the delivery system is carried out with the proximal tip portion at the retracted longitudinal length.

The majority of the proximal tip portion 50 may further comprise nylon, PET, a hydrophilically coated urethane, or other similar materials. It is desirable for the Shore hardness of the proximal tip portion 50 to be in the range of D30 to D65. The proximal tip portion may have a durometer of approximately 60 with a possible range of approximately 50 to 100. However, these properties may be substantially altered while retaining the same or similar results.

FIG. 8 illustratively depicts a proximal tip portion 50 from proximal end 51 to distal end 52. One embodiment of the proximal tip portion 50 may comprise the proximal end 51, the distal end 52, the interior void 53, the largest outside diameter 54, the extended longitudinal length 55, various retracted longitudinal lengths 56, 57, 58, 59, as shown in FIGS. 11 to 14, the first tapered portion 60, the second tapered portion 61, a proximal tip portion wall 62, undulations 63, a non-distensible balloon 64, a wall thickness 65, inserts 66, sections of modified stiffness 67, or any combination thereof.

The wall thickness 65 of the proximal tip portion 50 may vary throughout the proximal tip portion 50, and need not remain uniform throughout. Varying the wall thickness 65 may alter the stiffness of certain parts of the proximal tip portion 50 and allow the proximal tip portion 50 at the retracted longitudinal lengths 56, 57, 58, 59 to be arranged in a predetermined configuration. The stiffness of the proximal tip portion 50 may vary due to techniques other than varying the wall thickness 65. In general, the mean wall thickness 65 of the proximal tip portion 50 should be between 0.5 mm and 1.0 mm. At its thicker sections, the proximal tip portion 50 may have a wall thickness 65 of approximately 2.0 mm; and at its thinner sections, the proximal tip portion 50 may have a wall thickness 65 of approximately 0.2 mm. The longitudinal length of the proximal tip portion 50 at the extended longitudinal length 55 may be approximately 8 cm in length, although this longitudinal length may vary significantly. The largest outside diameter 54 of the proximal tip portion 50 at the extended longitudinal length 55 is generally approximately 6 mm, although this depends on the specific application or procedure for which the delivery system 40 is used. These dimensions are only examples and may deviate substantially given the situation. The dimensions are in no way intended to limit the scope of the invention to a specific size.

FIGS. 9 and 10 illustratively depict embodiments wherein the proximal tip portion 50 wall 62 comprises undulations 63. Undulations 63 may be utilized to encourage the proximal tip portion 50 at the retracted longitudinal lengths 56, 57, 58, 59, as shown in FIGS. 11 to 14, to be arranged in a predetermined configuration. Undulations 63 of the wall 62 may also be combined with other methods to vary the wall thickness 65 or the stiffness of the proximal tip portion 50, also resulting in the proximal tip portion 50 at the retracted longitudinal lengths 56, 57, 58, 59 to be arranged in a predetermined configuration. The term "predetermined," as used herein, does not imply that a specific configuration must be achieved after every transition to the retracted longitudinal lengths 56, 57, 58, 59.

In the embodiment depicted in FIG. 9, the undulations 63 comprise alternating sections of cylindrical and frusto-conical structures. Additional sections may be included in the sequence without degrading the results. Such a profile, upon an urging of the proximal end 51 of the proximal tip portion 50 in a proximal to distal direction, would encourage the frusto-conical sections to fold inward, while the cylindrical sections would tend to resist folding inward and remain in their original orientation. The combination of cylindrical and frusto-conical annular sections, combined with urging the proximal end 51 of the proximal tip portion 50 in a proximal to distal direction, may result in a proximal tip portion 50 at one of the retracted longitudinal lengths 56, 57, 58, 59 arranged in a predetermined configuration. FIG. 10 illustratively depicts another embodiment that would achieve the same or similar results as the embodiment depicted in FIG. 9. In this embodiment, depicted in FIG. 10, the undulations 63 are more curved and/or longitudinally continuous than the undulations 63 depicted in FIG. 9. Nonetheless, the undulations 63 of the wall 62 of the proximal tip portion 50 may enable the proximal tip portion 50 at the retracted longitudinal lengths 56, 57, 58, 59 to be arranged in a predetermined configuration. As depicted in FIGS. 8, 9, and 10, the longitudinal length is measured from the proximal end 51 to the distal end 52 of the proximal tip portion 50.

Figure 11:
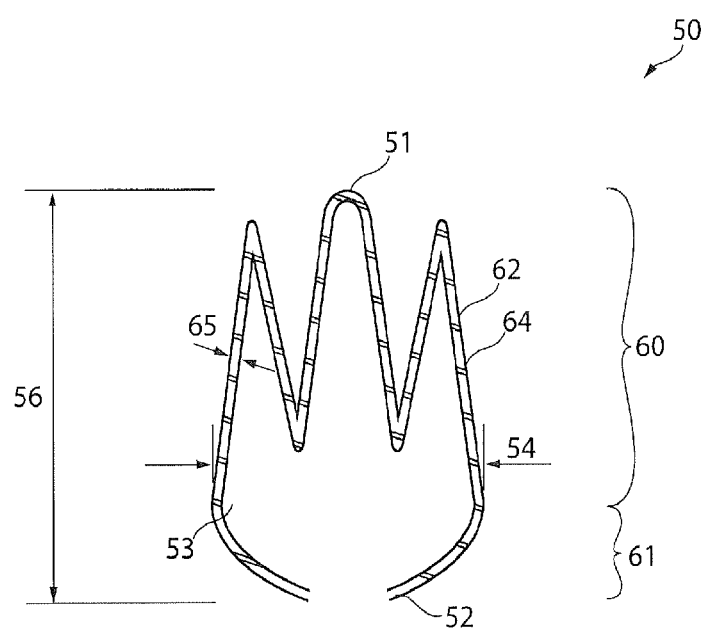
FIG. 11 is a side schematic view of a proximal tip portion at one exemplary retracted longitudinal length. The release mechanism and medical device carrier portion have been omitted for clarity of presentation.

The proximal tip portion 50 at the retracted longitudinal length 56 exhibiting a single set of folds is depicted in FIG. 11. The specific predetermined configuration of the proximal tip portion 50 is generally influenced by the physical properties of the proximal tip portion 50 before retraction. The embodiment depicted in FIG. 11 may be realized if the distal half of the first tapered portion 60 of the proximal tip portion 50 is stiffer than the proximal half of the first tapered portion 60. The distal half of first tapered portion 60 is more likely to invert than the proximal half, when the distal half is the stiffer of the two halves. A proximal tip portion 50 that exhibits only a single set of folds, as depicted in FIG. 11, provides a benefit because the longitudinal length from the distal end 52 to the proximal end 51 of the proximal tip portion 50 is less than the longitudinal length of the proximal tip portion 50 at the extended longitudinal length 55.

Figure 12:
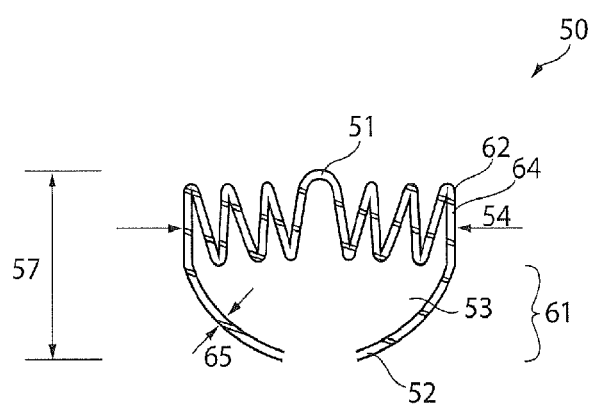
FIG. 12 is a side schematic view of a proximal tip portion at a retracted longitudinal length. The release mechanism and medical device carrier portion have been omitted for clarity of presentation.

Increasing the number of sets of folds exhibited by a proximal tip portion 50 at the retracted longitudinal length 57 may decrease the longitudinal length of the proximal tip portion 50 at the retracted longitudinal length 57. FIG. 12 illustratively depicts a proximal tip portion 50 at the retracted longitudinal length 57 with three sets of folds. The longitudinal length of the proximal tip portion 50 is measured from the distal end 52 to the proximal end 51 of the proximal tip portion 50. Although the proximal end 51 of the proximal tip portion 50 may not be the proximal-most point of the proximal tip portion 50, the longitudinal length is still measured from the distal end 52 to the proximal end 51 of the proximal tip portion 50. The embodiment depicted in FIG. 12 has three sets of folds, however the proximal tip portion 50 at the retracted longitudinal length 57 may have more or less than three sets of folds and still be beneficial. The exact number of folds exhibited by the proximal tip portion 50 at the longitudinal lengths 56, 57, 58, 59 is not crucial.

One embodiment of a proximal tip portion 50 at the retracted longitudinal length 57 is illustratively depicted in FIG. 12 and may be the corresponding retracted longitudinal length 57 to the proximal tip portion 50 at the extended longitudinal length 55 depicted in FIG. 9. The proximal tip portion 50 depicted in FIG. 12 comprises cylindrical sections connected by frusto-conical sections. Here, the cylindrical sections and frusto-conical sections become longitudinally closer upon the proximal tip portion 50 retracting. The specific shape and profile of the proximal tip portion 50 at the retracted longitudinal length 57 may be changed depending on the specific application of the delivery system 40 and may be influenced by the physical properties of the proximal tip portion 50 before retraction.

Figure 13:
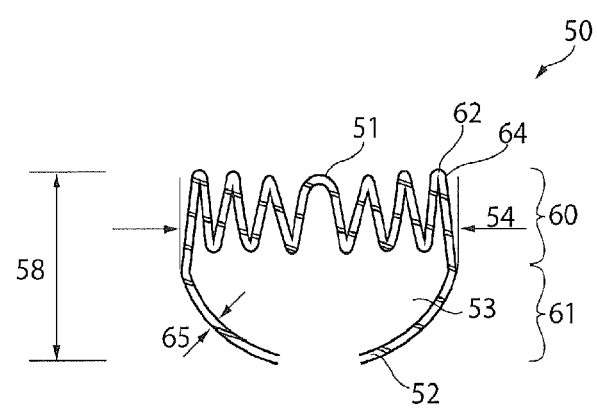
FIG. 13 is a side schematic view of a proximal tip portion at retracted longitudinal length. The release mechanism and medical device carrier portion have been omitted for clarity of presentation.

One embodiment of a proximal tip portion 50 at the retracted longitudinal length 58 is illustratively depicted in FIG. 13 may be the corresponding retracted longitudinal length 58 to the extended longitudinal length 55 illustratively depicted in FIG. 8, wherein the proximal tip portion 50 further comprises annular rings of varying stiffness. The stiffer annular rings of the proximal tip portion 50 will be less likely to invert when compared to the annular rings of the proximal tip portion 50 which are less stiff. It is possible that at the various retracted longitudinal lengths 56, 57, 58, that the proximal end 51 of the proximal tip portion 50 is not the proximal-most point of the proximal tip portion 50. However, even when such an event occurs, the proximal tip portion 50 will still be considered to be at the retracted longitudinal lengths 56, 57, 58 and a benefit, of being able to place a medical device in closer proximity to an obstruction, should still be realized.

Figure 14:
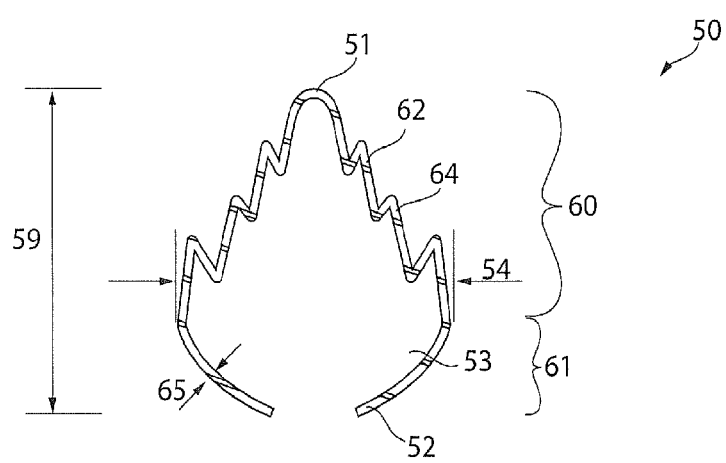
FIG. 14 is a side schematic view of a proximal tip portion at retracted longitudinal length. The release mechanism and medical device carrier portion have been omitted for clarity of presentation.

An embodiment of the proximal tip portion 50 at the retracted longitudinal length 59 is illustratively depicted in FIG. 14. As illustrated, it is not necessary that the proximal-most point of each set of folds be flush with any other set of folds, or with the proximal end 51 of the proximal tip portion 50, in order to realize a benefit.

Figure 15:
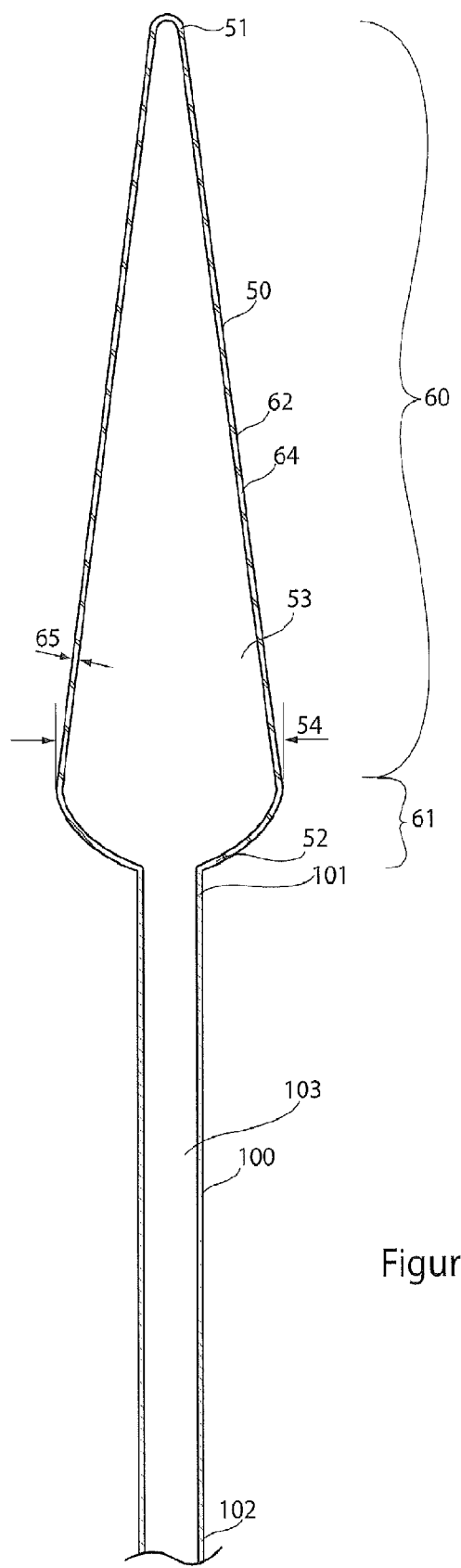
FIG. 15 is a side schematic view of a proximal end disposed and attached proximal to the medical device carrier member. The release mechanism has been omitted for clarity of presentation.

One embodiment of the carrier portion 100 and the proximal tip portion 50 is illustratively depicted in FIG. 15 with the release mechanism 120 omitted for clarity. This embodiment depicts the distal end 52 of the proximal tip portion 50 attached or otherwise coupled to the proximal end 101 of the carrier portion 100. Additionally, the interior void 53 of the proximal tip portion 50 communicates with the lumen 103 of the carrier portion 100 to allow fluid to travel from one section of the delivery system 40 to another. One method of use for this embodiment involves removing fluid from the lumen 103 at the distal end 102 of the carrier portion 100. This may create a negative gauge pressure at the interior void 53 of the proximal tip portion 50 thus encouraging the proximal tip portion 50 to transition from the extended longitudinal length 55 to one or more of the retracted longitudinal lengths 56, 57, 58, 59. This method assumes that the proximal tip portion 50 and carrier portion 100 are substantially fluid tight and that the fluid contained within the interior void 53 of the proximal tip portion 50 can only be removed through the lumen 103 of the medical device carrier portion.

Another method of use for this embodiment of the medical device delivery system 40 does not require the carrier portion 100 and the proximal tip portion 50 to be fluid tight. Instead, the carrier portion 100 and the proximal tip portion 50 need only be as fluid tight as is necessary to create sufficient negative gauge pressure within the interior void 53. The proximal tip portion 50 may transition from the extended longitudinal length 55 to one or more of the retracted longitudinal lengths 56, 57, 58, 59 when fluid is removed from the interior void 53 and through the lumen 103 of the carrier portion 100.

The fluid contained within the interior void 53 of the proximal tip portion 50 need not exit through the lumen 103 of the carrier portion 100. Other fluid removal methods and passages may be sufficient. Many types of fluids may be suitable for use within the delivery system 40, specifically within the interior void 53 of the proximal tip portion 50 and the lumen 103 of the carrier portion 100. Known candidates for fluids may include carbon dioxide, saline solution, the patient's own blood, or other such fluids known to those skilled in the arts.

Once the medical device 104 has been deployed at the desired anatomical site, it may be desirable for the proximal tip portion 50 to transition from the retracted longitudinal lengths 56, 57, 58, 59 to the extended longitudinal length 55 before any part of the delivery system 40 is removed from the patient. The extension process of the proximal tip portion 50 is generally a reverse of the retraction process. The same or a different fluid may be directed into the interior void 53 of the proximal tip portion 50, increasing the volume of the interior void 53 and correspondingly the longitudinal length of the proximal tip portion 50 as well. This fluid may be directed through the lumen 103 of the carrier portion 100, or by way of a different avenue. It is not necessary that the fluid be returned to the proximal tip portion 50 via the same avenue as it was removed; nor is it necessary that the fluid added to the interior void 53 be the same fluid or type of fluid that was removed from the interior void 53 of the proximal tip portion 50. It is not necessary that the proximal tip portion 50 be returned to an extended longitudinal length 55 before being withdrawn from the patient in order to gain the benefit of a delivery system 40 with a retractable proximal end. Furthermore, it may be desirable to fully withdraw the proximal tip portion 50, at either the extended longitudinal length 55 or the retracted longitudinal lengths 56, 57, 58, 59, through the lumen 83 of the containment sheath 80 before withdrawing the containment sheath 80 or any other part of the delivery system 40 from the patient.

Figure 16:
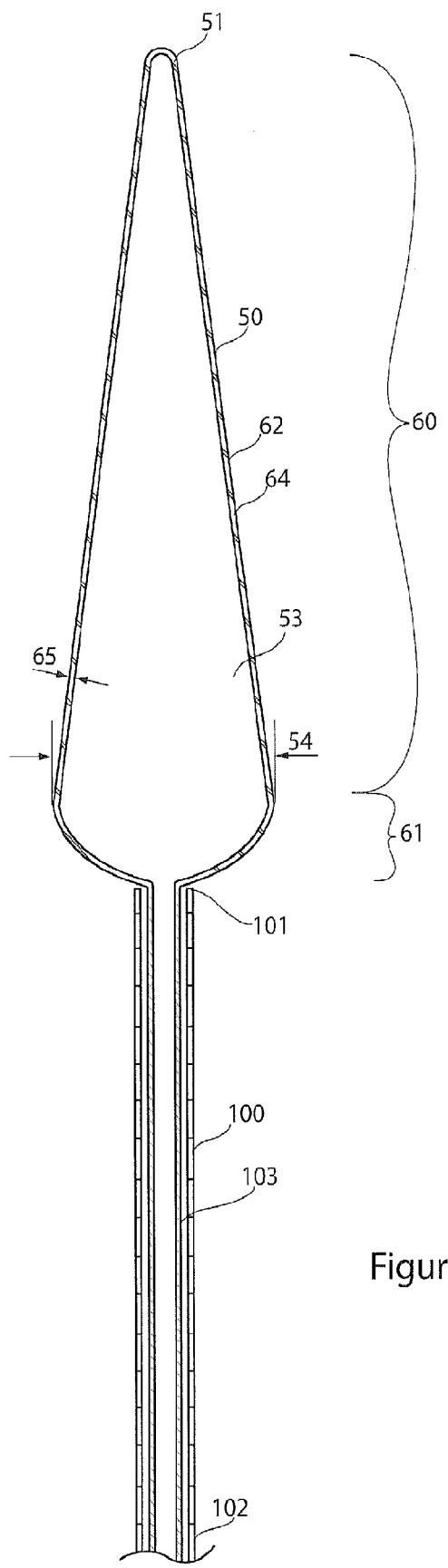
FIG. 16 is a side schematic view of a proximal end disposed proximal to medical device carrier member. The release mechanism has been omitted for clarity of presentation.

It is generally desirable for both the proximal tip portion 50 to transition from the extended longitudinal length 55 to the retracted longitudinal lengths 56, 57, 58, 59, and for the medial device carrier portion 100 to be advanced toward the proximal end 51 of the proximal tip portion 50. It may also be advantageous for the proximal tip portion 50 to be mounted separately from the carrier portion 100, as illustratively depicted in FIG. 16. In this embodiment, the proximal tip portion 50 may telescope and/or extend longitudinally away from the proximal end 101 of the carrier portion 100. Fluid traveling through the lumen 103 of the carrier portion 100 may require additional limitations to ensure that the fluid is adequately communicated to the interior void 53 of the proximal tip portion 50. Regardless of the exact mounting location of the proximal tip portion 50, a benefit is still received when the two aforementioned criteria are satisfied.

Figure 17:
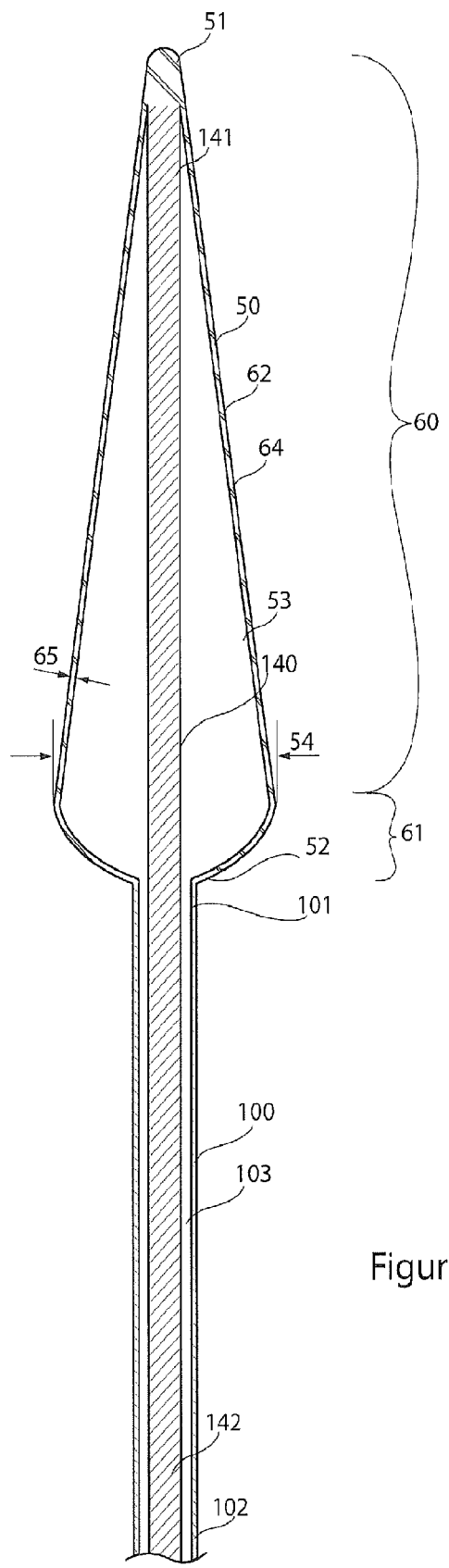
FIG. 17 is a side schematic view of a proximal tip portion, medical device carrier member, and mechanical actuator. The release mechanism has been omitted for clarity of presentation.

One embodiment comprises a fluid activator; while other embodiments may comprise alternate actuators to transition the proximal tip portion 50 between the extended longitudinal length 55 and the retracted longitudinal lengths 56, 57, 58, 59. Furthermore, an embodiment may receive benefit from comprising more than one actuator or more than one type of actuator. One embodiment, as illustratively depicted in FIG. 17, comprises a mechanical actuator 140 disposed within the lumen 103 of the carrier portion 100 which runs substantially parallel to the lumen 103. The proximal end 141 of the mechanical actuator 140 is attached or affixed or otherwise coupled to the proximal end 51 of the proximal tip portion 50. When the proximal tip portion 50 is at the extended longitudinal length 55 and the mechanical actuator 140 is urged in a proximal to distal direction, the proximal tip portion 50 transitions from the extended longitudinal length 55 toward the retracted longitudinal lengths 56, 57, 58, 59. When the proximal tip portion 50 is at one of the retracted longitudinal lengths 56, 57, 58, 59 and the mechanical actuator 140 is urged in a distal to proximal direction, the proximal tip portion 50 transitions from the retracted longitudinal lengths 56, 57, 58, 59 toward the extended longitudinal length 55. The mechanical actuator 140 may be urged in a proximal to distal direction, for instance, upon application of a tensile force applied longitudinally to some part of the mechanical actuator 140. The mechanical actuator 140 may be urged in a distal to proximal direction, for instance upon application of a compressive force applied longitudinally to some part of the mechanical actuator. During the application of these forces, it may be necessary to also apply a force to some portion of the carrier portion 100 in the direction opposite of the force applied to the mechanical actuator 140.

The embodiment depicted in FIG. 11 may also be a result of a proximal tip portion 50 having substantially uniform wall thickness 65, no undulations 63, no inserts 66, and no sections of modified stiffness 67, as depicted in FIG. 8. This embodiment may be a result of maintaining a positive gauge pressure in the interior void 53 of the proximal tip portion 50 while it is transitioning from the extended longitudinal length 55 to one or more of the retracted longitudinal lengths 56, 57, 58, 59 by way of a mechanical actuator 140. The positive gauge pressure would tend to keep the proximal tip portion 50 "inflated" and at a maximum volume and the mechanical actuator 140 would tend to move the proximal end 51 distally.

The mechanical actuator 140 may be comprised of stainless steel, a nickel-titanium alloy such as Nitinol, or any other suitable material or alloy having a flexibility adapted to navigate a patient's vasculature and strength sufficient to deliver an interventional device to the desired anatomical site.

Figure 18:
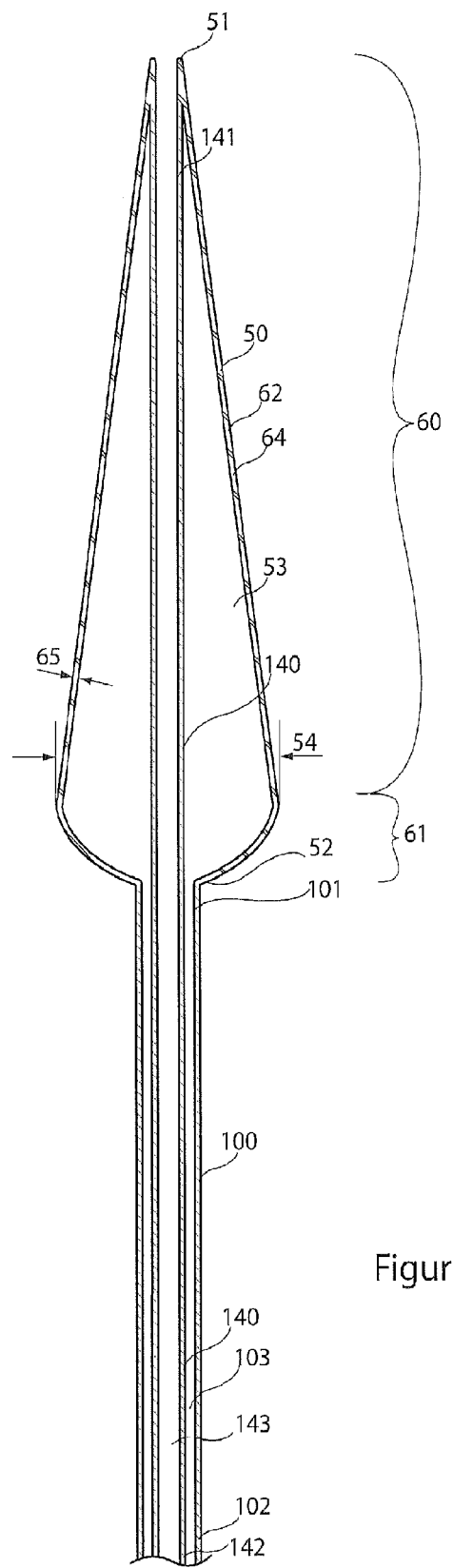
FIG. 18 is a side schematic view of a proximal tip portion, medical device carrier member, and mechanical actuator with longitudinally extending lumen. The release mechanism has been omitted for clarity of presentation.

An embodiment of the medical device delivery system 40 comprising a proximal tip portion 50, carrier portion 100, and mechanical actuator 140 with a lumen 143 extending longitudinally therein, is illustratively depicted in FIG. 18. The lumen 143 may extend throughout the duration of the mechanical actuator 140 and may be suitable for a medical device such as a wire guide. The wire guide may comprise a core member, which may be manufactured from any suitable material for use in an interventional procedure. For example, the core member may comprise stainless steel, a nickel-titanium alloy such as Nitinol, or any other suitable material or alloy having a flexibility adapted to navigate a patient's vasculature and strength sufficient to deliver an interventional device to a desired anatomical site. One example of a suitable wire guide is the 0.035" Lunderquist Extra Stiff Double Curved Exchange Wire Guide available from Cook Medical in Bloomington, Ind. The lumen 143 of the mechanical actuator 140 may be adapted to accommodate other medical devices.

The proximal tip portion 50 may transition between the extended longitudinal length 55 and the retracted longitudinal lengths 56, 57, 58, 59 via a fluid or mechanical actuator. The fluid or mechanical actuator may be replaced with an alternate actuator so long as the alternate actuator serves the same general function and operates in substantially the same manner. Alternate actuators may include a piezoelectric device or other actuators known to those skilled in the arts. A delivery system 40, comprising multiple actuators capable of transitioning the proximal tip portion 50 between the extended longitudinal length 55 and the retracted longitudinal lengths 56, 57, 58, 59, need not use every available actuator to effect this transition. A proximal tip portion 50 comprising a mechanical actuator 140 and a fluid actuator may utilize only one of these actuators to transition between the extended longitudinal length 55 and the retracted longitudinal lengths 56, 57, 58, 59.

Figure 19:
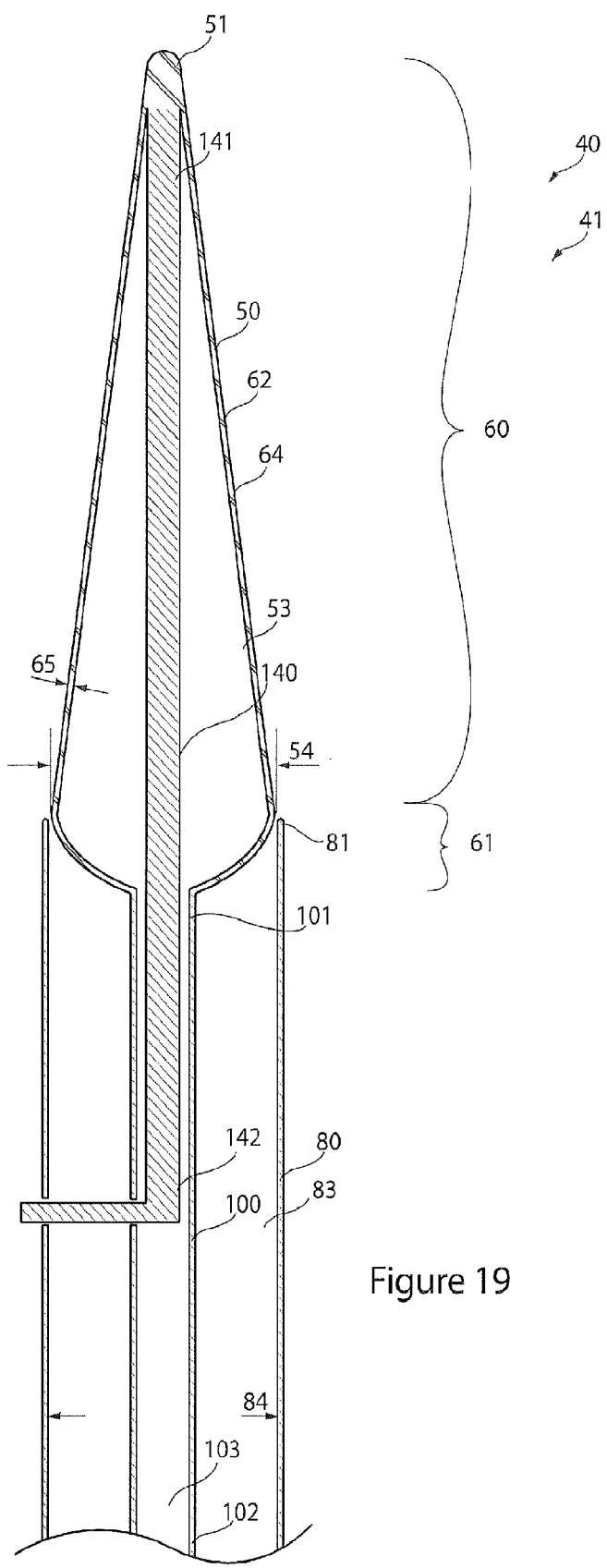
FIG. 19 is a side schematic view of a proximal tip portion, medical device carrier member, medical device containment sheath, and an mechanical actuator.

Another embodiment of a delivery system 40 comprising the proximal tip portion 50, carrier portion 100, and a mechanical actuator 140 are illustratively depicted in FIG. 19. The mechanical actuator 140 need not extend to the distalmost end (not shown) of the delivery system 40. The mechanical actuator 140 may be activated by a variety of elements which may comprise the medical device containment sheath 80. In this embodiment, the longitudinal, torsional, and/or lateral movement of the containment sheath 80 may effect a transition of the proximal tip portion 50 between the extended longitudinal length 55 and the retracted longitudinal lengths 56, 57, 58, 59. As well, the mechanical actuator 140 may be activated by a different part of the delivery system 40, or by an element not currently part of the delivery system 40.

The proximal tip portion 50 comprising a non-distensible balloon 64 and/or a non-compliant balloon may allow the proximal tip portion 50 to be extended or expanded without risk of changing the profile of the proximal tip portion 50 once it has been fully extended or expanded. In addition, varying the pressure and/or the volume of the fluid within the proximal tip portion 50 while it is in transit to or from the desired anatomical site may create variation in the rigidity of the proximal tip portion 50. Variation of the rigidity of the proximal tip portion 50 may be desirable to accommodate impediments within the interluminal vasculature including narrow vessels, tortuous vessels, occlusions, small radius turns, etc.

The structure of the proximal tip portion 50 may be modified to further comprise a radially extended profile and a radially retracted profile, wherein the radially extended profile has a larger cross-sectional area than the radially retracted profile. This modification may allow a medical device 104 to be placed closer to the aortic valve 26 as compared to a conventional medical device delivery system. If the proximal tip portion 50 does cross the aortic valve 26 during placement of a medical device 104 in the thoracic aorta 29, a proximal tip portion 50 exhibiting a radially retracted profile would present less interference with the aortic valve 26 and would thus be beneficial.

In one embodiment, the proximal tip portion 50 is at a neutral position at all or most of the longitudinal lengths including the extended longitudinal length 55 and the retracted longitudinal lengths 56, 57, 58, 59. At these lengths, if no outside forces, pressures, actuators, or other influences are imposed upon the proximal tip portion 50, it will tend to stay at its current length. However, other embodiments may benefit from the proximal tip portion 50 being at a neutral position at less than all of the longitudinal lengths. For instance, an embodiment of the proximal tip portion 50 may be at a neutral position at only the extended longitudinal length 55 such that when the proximal tip portion 50 is at any longitudinal length other than the extended longitudinal length 55, it will tend to transition toward the extended longitudinal length 55 without any outside forces, pressures, actuators, or other influences imposed upon it. In another embodiment, the proximal tip portion 50 may be at a neutral position at one or more of the retracted longitudinal lengths 56, 57, 58, 59, such that when the proximal tip portion 50 is at a longitudinal length other than the retracted longitudinal lengths 56, 57, 58, 59, it will tend to transition toward the retracted longitudinal lengths 56, 57, 58, 59 without any outside forces, pressures, actuators, or other influences imposed upon it. Different embodiments may be more beneficial than others depending on the specific context and location in which it is used. For instance, a proximal tip portion 50 with a neutral position at one of the retracted longitudinal lengths 56, 57, 58, 59 may be less likely to accidentally make contact with an obstruction, such as the aortic valve 26.

The neutral position of the proximal tip portion 50 may be set by a variety of means including, but not limited to: heat treatment, chemical treatment, casting, welding, ultrasound, etc. The neutral position may be set by adding elements to the proximal tip portion 50 such that the proximal tip portion ends to transition toward one or more longitudinal lengths. Furthermore, the neutral position may be set by increasing or decreasing the internal gauge pressure such that the mechanical actuator 140 used to transition the proximal tip portion, acts against the resistance created by the additional or diminished gauge pressure.

Figure 3:
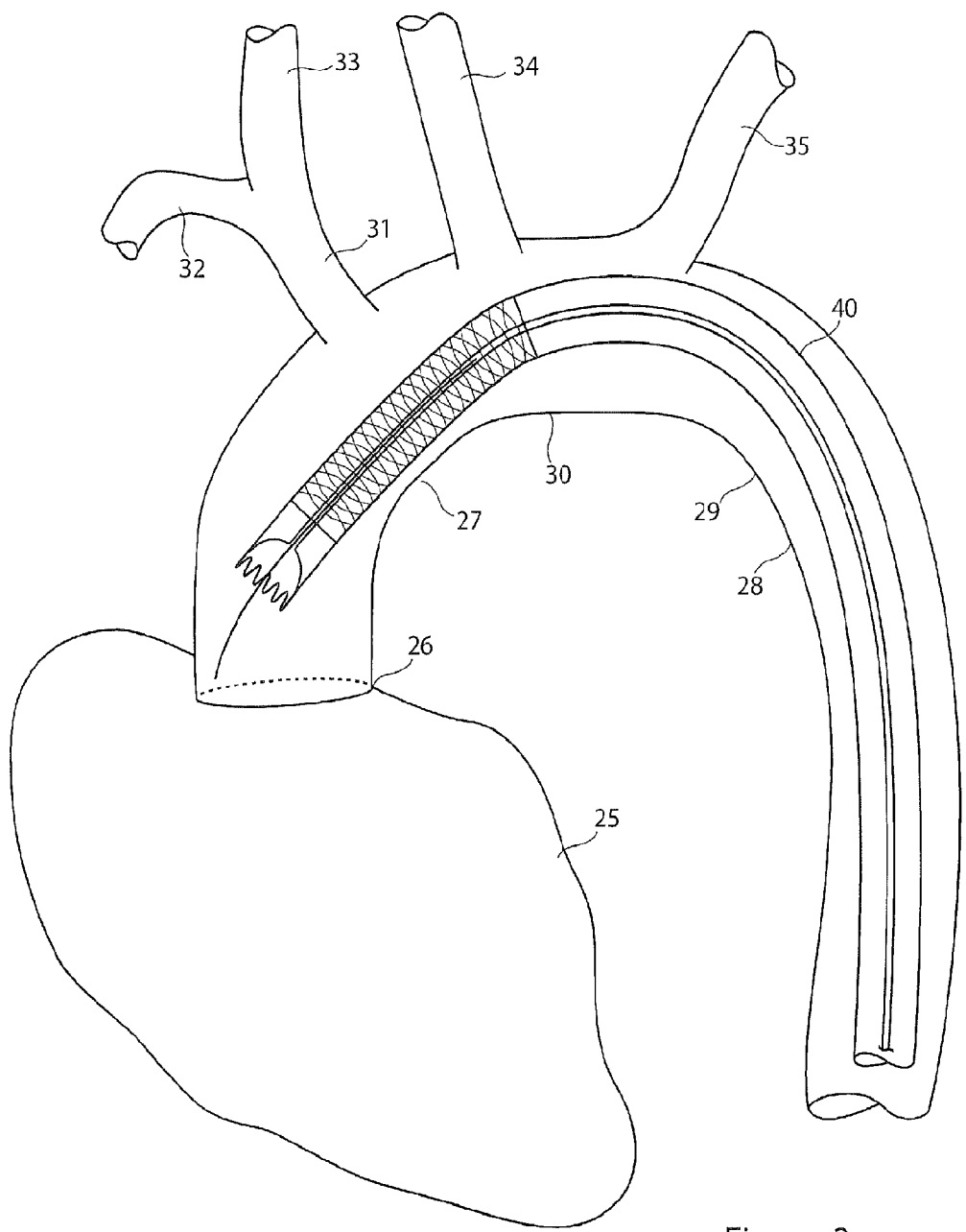
FIG. 3 is a front schematic view of an exemplary ascending and descending thoracic aorta with the proximal-most end of an embodiment at a retracted longitudinal length close to, but not crossing, the aortic valve.

One embodiment of the proximal tip portion 50, such as is depicted in FIG. 3 and FIG. 8, is not significantly curved, meaning that a central longitudinal axis is substantially straight. However, a curved proximal tip portion 50, such as one that comprises a curved central longitudinal axis, may also be retractable and exhibit an extended longitudinal length 55 and various retracted longitudinal lengths 56, 57, 58, 59. All of the methods of operation would be applicable and all of the same benefits could be realized from a longitudinally curved proximal tip portion 50.

At least part of the medical device delivery system 40, in particular, the proximal tip portion 50 may be radiopaque or comprise positional indicators, such as radiopaque or other types of markers that would be visible to the doctor during deployment. One or more parts of the delivery system 40 may be made radiopaque by, for example, varying the composition of the proximal tip portion 50 to include radiopaque ingredients, inserting radiopaque rings or strips within the material composing the proximal tip portion 50, or externally attaching or fastening radiopaque tags or markers on part of the delivery system 40. These markers are typically made of gold, tantalum, platinum, etc., but may comprise other materials.

The delivery system 40 may also be useful in other operations. For instance, one embodiment may also be useful for percutaneous aortic valves where a self-expanding valve is deployed via a catheter as opposed to open surgery. The proximal tip portion 50 could be at the expanded longitudinal length 55 during tracking and while crossing the aortic valve, but then transition to the retracted longitudinal length 56, 57, 58, 59 once the proximal end 41 of the delivery system 40 is in the ventricle of the heart 25 in order to avoid injury to the heart ventricle. In this instance, parts of the heart, namely the ventricle, would be the obstruction upon which no damage should be conferred.

Although the distal end 82 of the containment sheath 80, distal end 102 of the carrier portion 102, and distal end 142 of the mechanical actuator 140 may be depicted herein as being generally within one proximal tip portion 50 longitudinal length of the distal end 52 of the proximal tip portion 50, the aforementioned distal ends may and very likely will be significantly further from the proximal tip portion 50. The length depicted between the proximal tip portion 50 and these distal ends shall in no way imply relative lengths of the containment sheath 80, carrier portion 100, or mechanical actuator 140.

Figure 20:
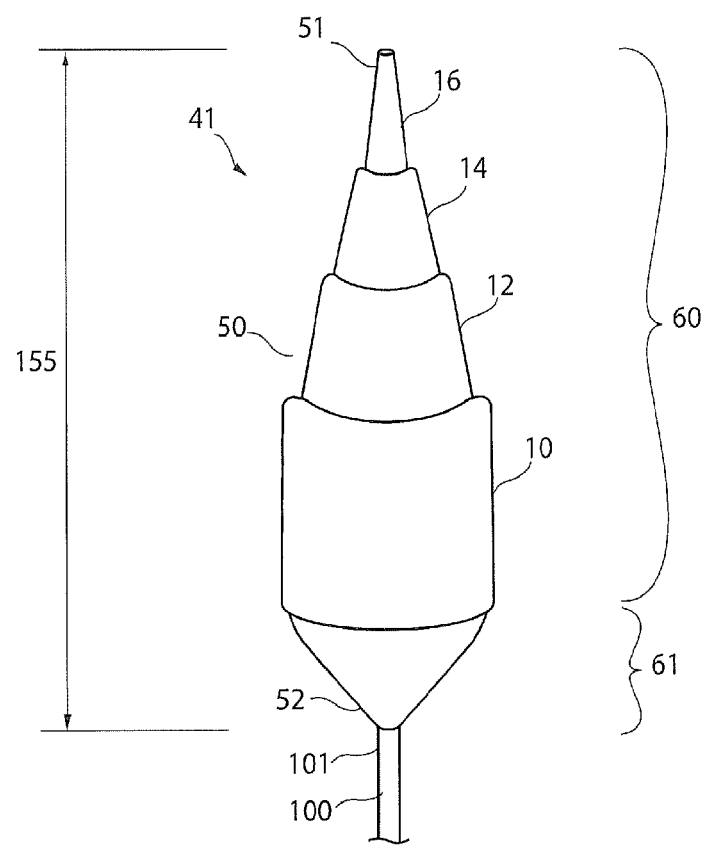
FIG. 20 is a side view of a telescopic proximal tip portion at an extended longitudinal length and a medical device carrier member.

FIG. 20 shows a view of a proximal end 41 of a further exemplary delivery system. A side view of a telescopic proximal tip portion 50 at an extended longitudinal length 155 and a medical device carrier portion 100 is shown. The proximal tip portion 50 comprises a first tapered portion 60 and a second tapered portion 61, the first tapered portion 60 further comprising first to fourth telescoping members 10, 12, 14, 16, the first telescoping member being the most distal telescoping member and the fourth telescoping member 16 being the most proximal telescoping member. The second tapered portion 61 is solid and is attached to the medical device carrier portion 100. The proximal tip portion 50 has a proximal end 51 at the proximal end of the first tapered portion 60 and a distal end 52 at the distal end of the second tapered portion 61. The medical device carrier portion 100 has a proximal end 101 attached to the distal end 52 of the proximal tip portion 50.

Figures 21, 22:
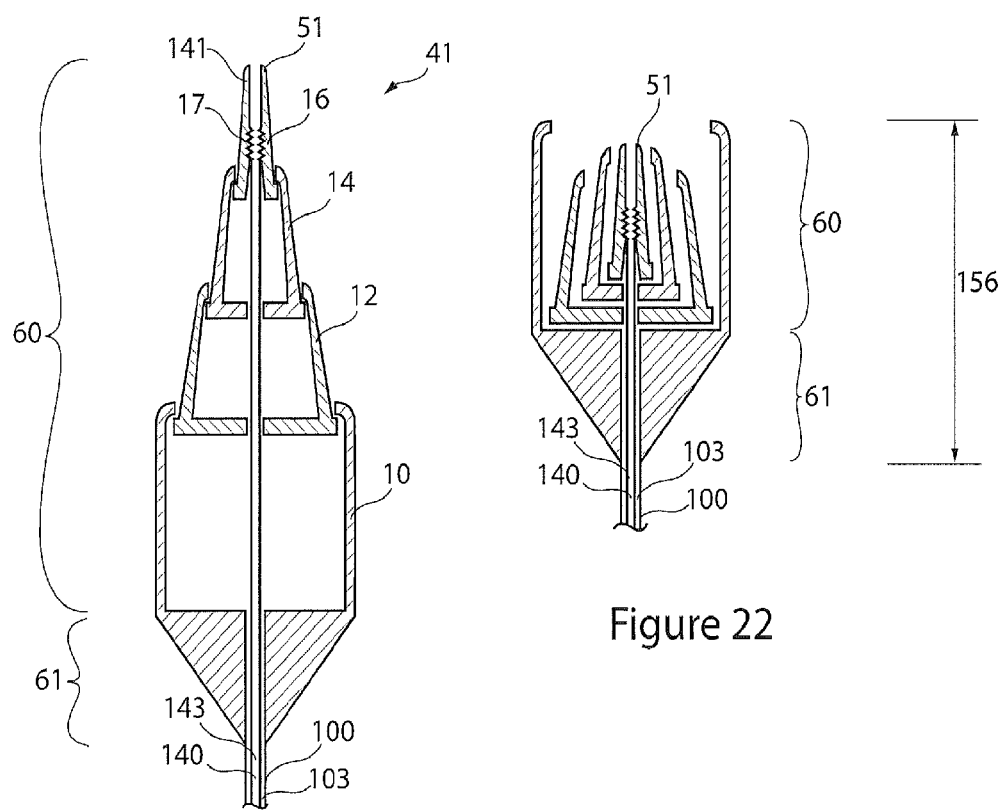
FIG. 21 is a side schematic view of the telescopic proximal tip portion and medical device carrier member of FIG. 20.
FIG. 22 is a side schematic view of the telescopic proximal tip portion and medical device carrier member of FIG. 20, the telescopic proximal tip portion at a retracted longitudinal length.

FIG. 21 shows a side schematic view of the telescopic proximal tip portion 50 and medical device carrier member of FIG. 20. The medical device carrier portion 100 comprises an inner lumen 103 extending longitudinally therein, which accommodates a mechanical actuator 140 having a proximal end 141, a distal end (not shown) and a lumen 143 through which a wire guide, for example, may extend longitudinally through. The mechanical actuator 140 is attached to the fourth telescoping member 16 by a screw thread 17. Other attachments, such as a glue joint etc., will be clear to the skilled person.

FIG. 22 shows a side schematic view of the telescopic proximal tip portion 50 and medical device carrier portion 100 of FIG. 20, the telescopic proximal tip portion 50 at a retracted longitudinal length 156. In the retracted configuration, each telescoping member fits within the telescoping member which was distal to it when the proximal tip portion 50 was in an extended longitudinal configuration.

As can be seen from FIGS. 20 to 22, the first telescoping member 10 is a straight sided member for housing the other telescoping members 12, 14, 16 when the proximal tip portion 50 is at a retracted longitudinal length 156. The second 12, third 14 and fourth 16 telescoping members are tapered towards the proximal end 51 of the proximal tip portion 50 so as to allow a surgeon to ease the proximal tip portion 50 through the vasculature of a patient. As can be seen from FIG. 21 the proximal inner diameter of each telescoping member is smaller than the distal outer diameter of the telescoping member arranged proximally to it so as to prevent the telescoping members from separating from one another, and to allow the members some relative movement to enable the tip to pass around curves. The material from which the members are made should be stiff enough to achieve these results. The overlapping edges of the telescoping members can be seen in FIG. 21. Preferably, the external edges of the telescoping members are rounded so as to reduce any damage to the patient's vasculature on transit therethrough.

The most proximal telescoping member, in this case the fourth telescoping member 16, comprises a floppy tip so as to minimize damage to the patient's vasculature on transit therethrough. The proximal end 51 of the proximal tip portion 50 is the proximal end of the floppy tip. The proximal end 51 is curved, again so as to minimize damage to the patient's vasculature on transit therethrough. The proximal end 51 of the floppy tip is bonded to the mechanical actuator 140. In some embodiments this may be sufficient to attach the mechanical actuator to the fourth telescoping member 16, without the need for screw thread 17. A wire guide may pass through the mechanical actuator 140 and out of the proximal end 51 of the proximal tip portion 50. The proximal tip portion 50 may be coated with a hydrophilic coating.

In another embodiment, the mechanical actuator 140 may terminate at the screw thread 17 or other attachment. In this case the part of the proximal tip portion proximal to the screw joint 17 may be just floppy tip material. This may be advantageous in reducing trauma to the vasculature.

In order to actuate movement of the proximal tip portion between extended 155 and retracted 156 longitudinal lengths, the distal end of the mechanical actuator 140 can be pulled distally, sliding through the medical device carrier portion 100, to pull the proximal tip 51 of the proximal tip portion 50 towards the medical device carrier portion 100 as described hereinbefore.

Although a telescoping proximal tip portion having four telescoping members is shown, it will be clear to the skilled person that any number of telescoping members may be used. The second tapered portion 61, described as solid and attached to the medical device carrier portion 100, may be hollow and/or may be separate from the medical device carrier portion 100. In fact, a medical device (not shown) retained on the medical device carrier portion 100 may act as a stop against which the second tapered portion 61 of the proximal tip portion rests whilst the proximal tip portion 50 is retracted from an extended longitudinal length to a retracted longitudinal length. Furthermore, as described above, the proximal tip portion 50 may be retracted from an extended longitudinal length to a retracted longitudinal length by means of a mechanical actuator as shown, a fluid actuating apparatus as described above, or a combination of both.

Figure 23:
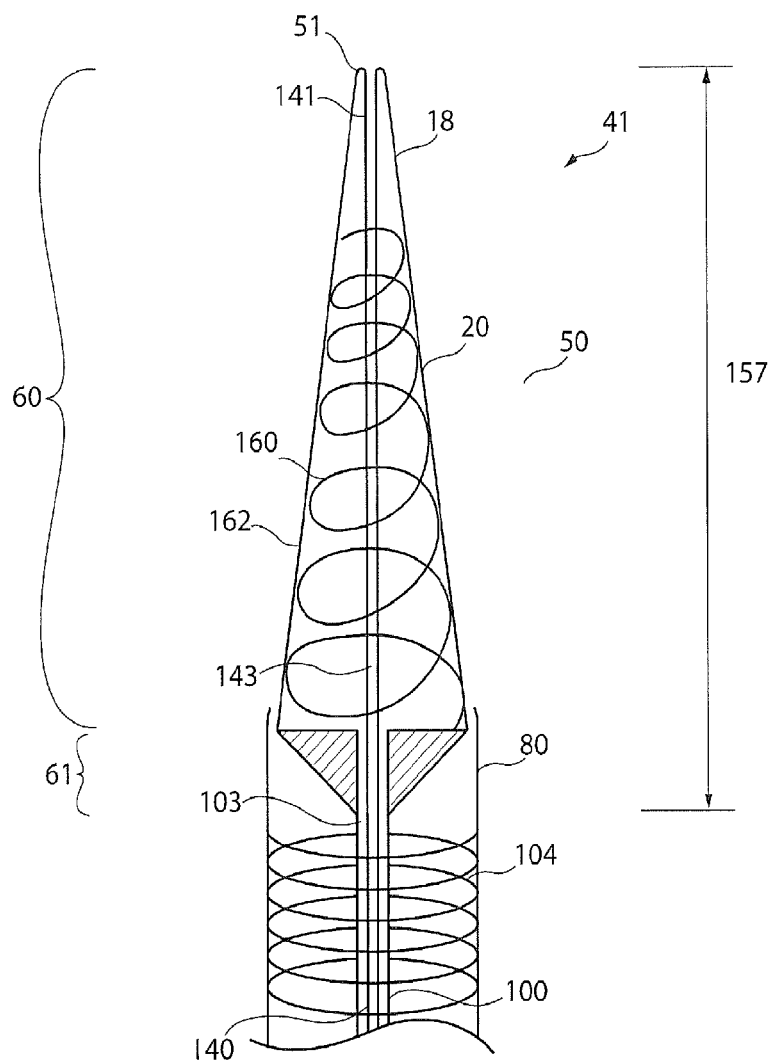
FIG. 23 is a side schematic view of a sprung proximal tip portion at an extended longitudinal length, a medical device carrier member and a medical device containment sheath.

FIG. 23 shows a side schematic view of a sprung proximal tip portion 50 at an extended longitudinal length 157, a medical device carrier portion 100 and a medical device containment sheath 80. A medical device 104 is mounted on the medical device carrier member 104, within the sheath 80. The sprung proximal tip portion 50 comprises a first tapered portion 60 and a second tapered portion 61. The first tapered portion 60 further comprises a sprung portion 20 and a flexible tip 18, the flexible tip 18 arranged proximally of the sprung portion 20. The sprung portion 20 comprises a spring 160 and a low friction covering 162, such as ePTFE, which covers the spring 160. The second tapered portion 61 is solid and is attached to the medical device carrier portion 100. The proximal tip portion 50 has a proximal end 51 at the proximal end of the first tapered portion 60 and a distal end 52 at the distal end of the second tapered portion 61. The medical device carrier member has a proximal end 101 attached to the distal end 52 of the proximal tip portion 50.

The floppy tip 18 is included to reduce damage to the patient's vasculature on transit therethrough. The proximal end 51 of the proximal tip portion 50 is the proximal end of the floppy tip 18. The proximal end 51 is curved, again so as to minimize damage to the patient's vasculature on transit therethrough and is bonded to the mechanical actuator 140. The floppy tip portion 18 is bonded at its distal end to the low friction covering 161 of the sprung portion 20 of the proximal tip portion 50.

As described hereinbefore, the second tapered portion 61 may be hollow and/or may be separate from the medical device carrier portion 100. Where the second tapered portion 61 is hollow, it may provide a space for the spring to compress into, thus enabling a greater reduction in the longitudinal length of the proximal tip portion 50.

Figure 24:
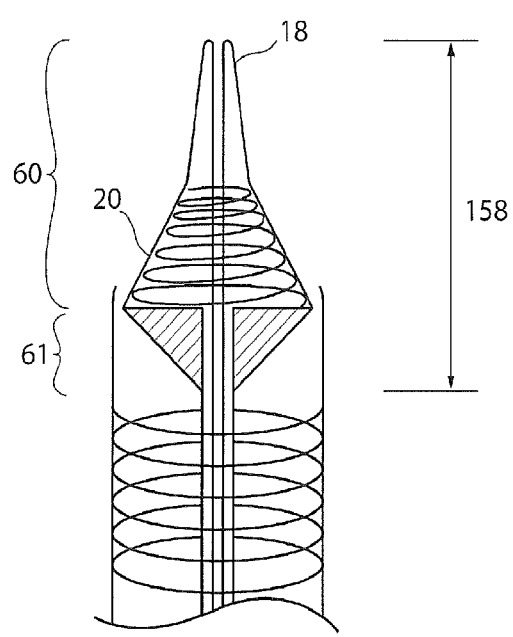
FIG. 24 is a side schematic view of the sprung proximal tip portion, medical device carrier member and medical device containment sheath of FIG. 23, the sprung proximal tip portion at a retracted longitudinal length.

FIG. 24 shows a side schematic view of the sprung proximal tip portion 50, medical device carrier portion 100 and medical device containment sheath 80 of FIG. 23 where the sprung proximal tip portion 50 is at a retracted longitudinal length 158. The spring 160 is compressed by pulling distally on the mechanical actuator 140. In turn this action pulls the proximal end 51 of the proximal tip portion towards the medical device carrier portion 100 and thus retracts the proximal tip portion 50 into a retracted longitudinal length 158.

Figure 25:
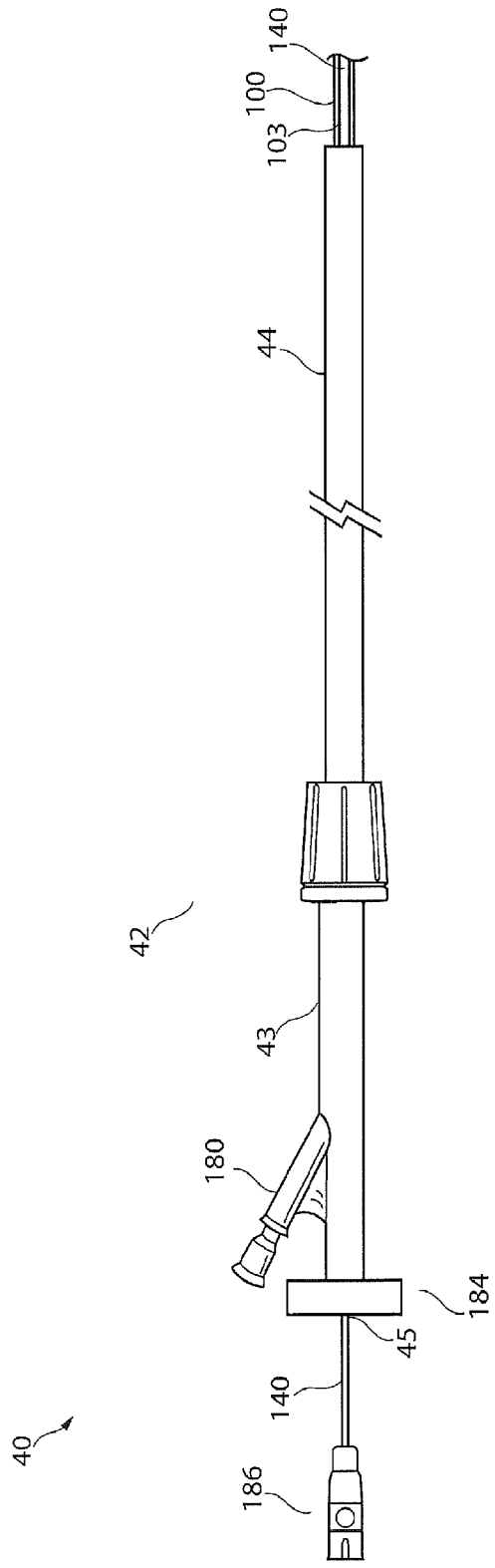
FIG. 25 shows an exemplary handle of a delivery system having a proximal tip portion as described herein.

FIG. 25 shows an exemplary distal portion 42 of a delivery system 40 having a proximal tip portion which may be actuated by, for example, a mechanical actuator, a fluid actuator, or a combination of actuators. The distal portion 42 of the delivery system comprises an elongate handle 43 and an elongate pusher 44. The handle 43 extends from the distal end of the delivery device 40 to the pusher 44, which is arranged proximal of the handle. The pusher terminates distal of the medical device 104 on the medical device carrier portion, and thus distal of the proximal tip portion 50. The pusher 44 is used for releasing a medical device from the medical device carrier portion 100 and for, in some embodiments, holding the distal end of the proximal tip portion steady whilst the proximal end of the proximal tip portion is retracted.

The elongate handle 43 and pusher 44 both comprise a lumen (not shown) for passage of a medical device carrier portion 100, and thus mechanical actuator 140, therein. The lumen of the handle 43 has a first opening 45 at a distal end of the handle 43 and a second opening (not shown) at the proximal end of the handle 43. The first opening may receive the mechanical actuator 140, which may pass inside the lumen of the handle, through a medical device carrier portion contained therein. The first opening may be sealed by a Tuohy Borst 184 rotating valve, which enables the mechanical actuator to be secured relative to the handle when the proximal tip portion is in the extended longitudinal position and moveable relative to the handle whilst the proximal tip portion is retracted. At the distal end of the mechanical actuator 140 is a Luer fitting 186. The second opening is in fluid communication with the lumen of the pusher 44. A third opening in the lumen of the handle 43, between the first and second openings, is connected to an inflation port 180 for allowing fluid to enter the lumen 103 of the medical device carrier portion 100. Such fluid may be used for inflating and/or deflating the proximal tip portion of the delivery system 40. Where the proximal tip portion uses only mechanical actuation, the inflation port may not be required.

The skilled person will understand that features described with reference to particular embodiments may be combined with one another.

While various embodiments have been described, it will be apparent to those of ordinary skill in the art that many more embodiments and implementations are possible. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

The invention claimed is:

1. A medical device delivery system comprising:
   a medical device carrier portion comprising a proximal end;
   a release mechanism cooperating with said medical device carrier portion and operable to release a medical device from said medical device carrier portion; and
   an elongate proximal tip comprising the most proximal end of the medical device delivery system, a largest outside diameter, a proximal end, a distal end, and a plurality of longitudinal lengths as measured from said proximal end to said distal end of said elongate proximal tip, said proximal tip further comprises and is operable between at least an extended longitudinal length and a retracted longitudinal length of said plurality of longitudinal lengths, wherein said extended longitudinal length is greater than said retracted longitudinal length, wherein the longitudinal length of said proximal end of said proximal tip varies between said extended longitudinal length and said retracted longitudinal length, wherein said proximal tip is disposed proximal to said medical device carrier portion in both said extended longitudinal length and said retracted longitudinal length, and wherein at least a portion of the proximal tip is collapsible within itself.

2. The medical device delivery system as in claim 1, wherein when said proximal tip is operated from said extended longitudinal length toward said retracted longitudinal length, said proximal end of said medical device carrier portion is longitudinally advanced toward said proximal end of said proximal tip.

3. The medical device delivery system according to claim 1, wherein said largest outside diameter of said proximal tip at said retracted longitudinal length is at most substantially equal to said largest outside diameter of said proximal tip at said extended longitudinal length.

4. The medical device delivery system according to claim 1, wherein said proximal tip further comprises an interior void, said medical device carrier portion further comprises a first lumen extending longitudinally therein, said first lumen of said medical device carrier portion communicates with said interior void of said proximal tip, and wherein said proximal tip transitions between said extended longitudinal length and said retracted longitudinal length upon a change in volume of a fluid contained within said interior void of said proximal tip.

5. The medical device delivery system according to claim 1, wherein said proximal tip further comprises a non-distensible balloon.

6. The medical device delivery system according to claim 1, wherein said medical device delivery system further comprises a mechanical actuator disposed distal to said proximal end of said proximal tip, wherein said mechanical actuator is capable of transitioning said proximal tip between said extended longitudinal length and said retracted longitudinal length upon application of a force applied longitudinally to said mechanical actuator and transmitted to said proximal end.

7. The medical device delivery system according to claim 1, wherein the medical device delivery system further comprises a medical device containment sheath, and said largest outside diameter of said proximal tip at said extended a longitudinal length is at most substantially equal to an inside diameter of the medical device containment sheath.

8. The medical device delivery system according to claim 1, wherein said medical device delivery system further comprises a medical device, said medical device is disposed concentric to said medical device carrier portion.

9. The medical device delivery system as in claim 8, wherein said medical device comprises a stent-graft.

10. The medical device delivery system according to claim 1, wherein said proximal tip further comprises a wall comprising a plurality of undulations, wherein said proximal tip at said retracted longitudinal length is arranged in a predetermined configuration.

11. The medical device delivery system according to claim 10, wherein said plurality of undulations comprises longitudinally alternating cylindrical sections and frusto-conical sections.

12. The medical device delivery system according to claim 1, wherein said proximal tip further comprises longitudinally alternating sections, wherein a first set of sections of said longitudinally alternating sections is stiffer than a second set of sections of said longitudinally alternating sections.

13. The medical device delivery system as in claim 1, wherein said proximal tip further comprises a wall thickness and a plurality of longitudinally alternating sections, wherein said wall thickness of a first set of sections of said plurality of longitudinally alternating sections is greater than said wall thickness of an alternate set of sections of said plurality of longitudinally alternating sections.

14. A medical device delivery system comprising:
   a medical device carrier portion comprising a proximal end and a first lumen extending longitudinally therein;
   a release mechanism cooperating with said medical device carrier portion and operable to release a medical device from said medical device carrier portion;
   a mechanical actuator comprising a first lumen extending longitudinally therein and disposed in said first lumen of said medical device carrier portion; and a single proximal tip comprising the proximal most end of the medical delivery system, a largest outside diameter, a proximal end, a distal end, and a plurality of longitudinal lengths as measured from said proximal end to said distal end of said proximal tip, said proximal tip further comprises and is operable between at least an extended longitudinal length and a retracted longitudinal length of said plurality of longitudinal lengths, wherein said extended longitudinal length is greater than said retracted longitudinal length, wherein the longitudinal length of said proximal end of said proximal tip varies between said extended longitudinal length and said retracted longitudinal length, wherein said proximal tip is disposed proximal to said medical device carrier portion in both the extended longitudinal length and the retracted longitudinal length, and wherein at least a portion of the proximal tip is collapsible within itself.

15. A medical device delivery system according to claim 14, wherein when said proximal tip is operated from said extended longitudinal length toward said retracted longitudinal length, said proximal end of said medical device carrier portion is longitudinally advanced toward said proximal end of said proximal tip.

16. The medical device delivery system according to claim 14, wherein said largest outside diameter of said proximal tip at said retracted longitudinal length is at most substantially equal to said largest outside diameter of said proximal tip at said extended longitudinal length.

17. The medical device delivery system according to claim 14, wherein said proximal tip further comprises an interior void communicating with said first lumen of said medical device carrier portion, and wherein said proximal tip transitions between said extended longitudinal length and said retracted longitudinal length upon a change in volume of a fluid contained within said interior void of said proximal tip.

18. The medical device delivery system according to claim 14, wherein said mechanical actuator further comprises a proximal end, said proximal tip further comprises a distal end, said proximal tip transitions from said extended longitudinal length to said retracted longitudinal length upon application of a tensile force applied longitudinally to said mechanical actuator and transmitted to said proximal end of said proximal end; and upon application of a compressive force applied longitudinally to said medical device carrier portion and transmitted to said distal end of said proximal end portion.

19. The medical device delivery system according to claim 14, wherein said mechanical actuator further comprises a proximal end, said proximal tip further comprises a distal end, said proximal tip transitions from said retracted longitudinal length to said extended longitudinal length upon application of a compressive force applied longitudinally to said mechanical actuator and transmitted to said proximal end of said proximal end portion; and upon application of a tensile force applied longitudinally to said medical device carrier portion and transmitted to said distal end of said proximal end portion.

20. A method of delivering a medical device comprising:
providing a medical device delivery system with a medical device carrier portion comprising a proximal end, and a proximal tip comprising the proximal most end of the delivery system, a largest outside diameter, a proximal end, a distal end, and a plurality of longitudinal lengths as measured from said proximal end to said distal end of said proximal tip, and wherein said proximal tip is disposed proximal to said medical device carrier portion in both the extended longitudinal length and the retracted longitudinal length;
locating the proximal tip in a patient, proximate a treatment site, the proximal tip in its extended longitudinal length; and
operating the proximal tip from its extended longitudinal length to its retracted longitudinal length; wherein at least a portion of the proximal tip is collapsible within itself.

* * * * *